US006369091B1

(12) United States Patent
Sircar et al.

(10) Patent No.: US 6,369,091 B1
(45) Date of Patent: *Apr. 9, 2002

(54) BENZIMIDAZOLE ANALOGS AS DOWN-REGULATORS OF IGE

(75) Inventors: Jagadish C. Sircar, San Diego; Mark L. Richards, La Jolla, both of CA (US); Michael G. Campbell, Durham, NC (US); Michael W. Major, Glendale, WI (US)

(73) Assignee: Avanir Pharmaceuticals, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/422,304

(22) Filed: Oct. 21, 1999

Related U.S. Application Data

(63) Continuation-in-part of application No. 09/316,870, filed on May 21, 1999.
(60) Provisional application No. 60/086,494, filed on May 21, 1998.

(51) Int. Cl.$^7$ ............................................. A61K 31/415
(52) U.S. Cl. ....................................................... 514/394
(58) Field of Search ............................................ 514/394

(56) References Cited

U.S. PATENT DOCUMENTS 6,153,631 A * 11/2000 Petrie et al. ................ 514/367

FOREIGN PATENT DOCUMENTS

| EP | 0 221 346 | 5/1987 |
|----|-----------|--------|
| EP | 0 232 199 A | 8/1987 |
| EP | 0 469 477 | 2/1992 |
| EP | 0 497 564 | 8/1992 |
| EP | 0 700 906 A | 3/1996 |
| EP | 0 719 765 A | 7/1996 |
| EP | 0 719 765 | 7/1996 |
| WO | WO 90 09989 | 9/1990 |
| WO | WO 93 25517 | 12/1993 |
| WO | WO 98 17267 | 4/1998 |

OTHER PUBLICATIONS

S. Kanag'ozov, Synthesis of N–acyl derivatives of 6–amino–1–4–benzodioxane STN International, vol. 39, No. 1989 pp. 5–8, Abstract only.
Ashton et al., "Now low–density lipoprotein receptor upregulators acting via a novel mechanism", Journal of Medicinal Chemistry, vol. 39, Jan. 1, 1996, pp. 3343–3356.
B. V. Cheney et al., "Structure–activity correlations for a series of antiallergy agents. 3. Development of a quantitative model", Journal Med. Chem, vol. 26, No. 5, 1983, pp. 726–737.
I Yildir, "Synthesis of 2–(substitutedphenyl) benzimidazole derivatives and their sedative activity: Structure–activity relationship", Journal Fax. Gazi Univ., vol. 7, No. 2, 1990, pp. 111–114.

* cited by examiner

Primary Examiner—Theodore J. Criares
Assistant Examiner—Jennifer Kim
(74) Attorney, Agent, or Firm—Knobbe, Martens, Olson & Bear, LLP

(57) ABSTRACT

This invention relates to a family of diacyl benzimidazole analogs, which are inhibitors of the IgE response to allergens. These compounds are useful in the treatment of allergy and/or asthma or any diseases where IgE is pathogenic.

18 Claims, No Drawings

BENZIMIDAZOLE ANALOGS AS DOWN-REGULATORS OF IGE

RELATED APPLICATIONS

This application is a continuation-in-part application of pending U.S. patent application Ser. No. 09/316,870, filed on May 21, 1999, which claims priority under 35 U.S.C. §119(e) to U.S. Provisional Application No. 60/086,494, filed on May 21, 1998.

BACKGROUND OF THE INVENTION

This invention relates to small molecule inhibitors of the IgE response to allergens that are useful in the treatment of allergy and/or asthma or any diseases where IgE is pathogenic.

An estimated 10 million persons in the United States have asthma, about 5% of the population. The estimated cost of asthma in the United States exceeds $6 billion. About 25% of patients with asthma who seek emergency care require hospitalization, and the largest single direct medical expenditure for asthma has been inpatient hospital services (emergency care), at a cost of greater than $1.6 billion. The cost for prescription medications, which increased 54% between 1985 and 1990, was close behind at $1.1 billion (Kelly, *Pharmacotherapy* 12:13S–21S (1997)).

According to the National Ambulatory Medical Care Survey, asthma accounts for 1% of all ambulatory care visits, and the disease continues to be a significant cause of missed school days in children. Despite improved understanding of the disease process and better drugs, asthma morbidity and mortality continue to rise in this country and worldwide (U.S. Departmnent of Health and Human Services; 1991, publication no. 91–3042). Thus, asthma constitutes a significant public health problem.

The pathophysiologic processes that attend the onset of an asthmatic episode can be broken down into essentially two phases, both marked by bronchoconstriction, that causes wheezing, chest tightness, and dyspnea. The first, early phase asthmatic response is triggered by allergens, irritants, or exercise. Allergens cross-link immunoglobulin E (IgE) molecules bound to receptors on mast cells, causing them to release a number of pre-formed inflammatory mediators, including histamine. Additional triggers include the osmotic changes in airway tissues following exercise or the inhalation of cold, dry air. The second, late phase response that follows is characterized by infiltration of activated eosinophils and other inflammatory cells into airway tissues, epithelial desquamonon, and by the presence of highly viscous mucus within the airways. The damage caused by this inflammatory response leaves the airways "primed" or sensitized, such that smaller triggers are required to elicit subsequent asthma symptoms.

A number of drugs are available for the palliative treatment of asthma; however, their efficacies vary markedly. Short-acting $\beta_2$-adrenergic agonists, terbutaline and albuterol, long the mainstay of asthma treatment, act primarily during the early phase as bronchodilators. The newer long-acting $\beta_2$-agonists, salmeterol and formoterol, may reduce the bronchoconstrictive component of the late response. However, because the $\beta_2$-agonists do not possess significant antiinflammatory activity, they have no effect on bronchial hyperreactivity.

Numerous other drugs target specific aspects of the early or late asthmatic responses. For example, antihistamines, like loratadine, inhibit early histamine-mediated inflammatory responses. Some of the newer antihistamines, such as azelastine and ketotifen, may have both antiinflammatory and weak bronchodilatory effects, but they currently do not have any established efficacy in asthma treatment. Phosphodiesterase inhibitors, like theophylline/xanthines, may attenuate late inflammatory responses, but there is no evidence that these compounds decrease bronchial hyperreactivity. Anticholinergics, like ipratopium bromide, which are used in cases of acute asthma to inhibit severe bronchoconstriction, have no effect on early or late phase inflammation, no effect on bronchial hyperreactivity, and therefore, essentially no role in chronic therapy.

The corticosteroid drugs, like budesonide, are the most potent antiinflammatory agents. Inflammatory mediator release inhibitors, like cromolyn and nedocromil, act by stabilizing mast cells and thereby inhibiting the late phase inflammatory response to allergen. Thus, cromolyn and nedocromil, as well as the corticosteroids, all reduce bronchial hyperreactivity by minimizing the sensitizing effect of inflammatory damage to the airways. Unfortunately, these antiinflammatory agents do not produce bronchodilation.

Several new agents are currently being developed that inhibit specific aspects of asthmatic inflammation. For instance, leukotriene receptor antagonists (ICI-204, 219, accolate), specifically inhibit leukotriene-mediated actions. The leukotrienes have been implicated in the production of both airway inflammation and bronchoconstriction.

Thus, while numerous drugs are currently available for the treatment of asthma, these compounds are primarily palliative and/or have significant side effects. Consequently, new therapeutic approaches which target the underlying cause rather than the cascade of symptoms would be highly desirable. Asthma and allergy share a common dependence on IgE-mediated events. Indeed, it is known that excess IgE production is the underlying cause of allergies in general and allergic asthma in particular (Duplantier and Cheng, *Ann. Rep. Med. Chem.* 29:73–81 (1994)). Thus, compounds that lower IgE levels may be effective in treating the underlying cause of asthma and allergy.

None of the current therapies eliminate the excess circulating IgE. The hypothesis that lowering plasma IgE may reduce the allergic response, was confirmed by recent clinical results with chimeric anti-IgE antibody, CGP-51901, and recombinant humanized monoclonal antibody, rhuMAB-E25. Indeed, three companies, Tanox Biosystems, Inc., Genentech Inc. and Novartis AG are collaborating in the development of a humanized anti-IgE antibody (BioWorld® Today, Feb. 26, 1997, p. 2) which will treat allergy and asthma by neutralizing excess IgE. Tanox has already successfully tested the anti-IgE antibody, CGP-51901, which reduced the severity and duration of nasal symptoms of allergic rhinitis in a 155-patient Phase II trial (Scrip #2080, Nov. 24, 1995, p.26). Genentech recently disclosed positive results from a 536 patient phase-II/III trials of its recombinant humanized monoclonal antibody, rhuMAB-E25 (BioWorld®) Today, Nov. 10, 1998, p. 1). The antibody, rhuMAB-E25, administered by injection (highest dose 300 mg every 2 to 4 weeks as needed) provided a 50% reduction in the number of days a patient required additional "rescue" medicines (antihistimines and decongestants), compared to placebo. An NDA filing for this product is projected to be in the year 2000. The positive results from anti-IgE antibody trials suggest that therapeutic strategies aimed at IgE down-regulation may be effective.

SUMMARY OF THE INVENTION

The present invention discloses a family of related compounds for use in the treatment of a condition associated with an excess IgE level. The benzimidazole inhibitors of IgE in accordance with the present invention are represented by the generic formula:

Structure 1(A)

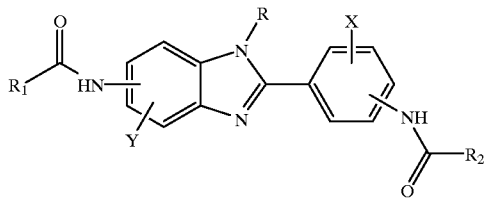

X and Y are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$. R is selected from the group consisting of H, $CH_3$, $C_2H_5$, $C_3H_7$, $C_4H_9$, $CH_2Ph$, and $CH_2C_6H_4$—F(p-). $R_1$ and $R_2$ are independently selected from the group consisting of alkyl, cycloalkyl substituted cycloalkyl, multi-ring cycloalkyl, fused-ring aliphatic, cyclopropyl, substituted cyclopropyl, cyrlobutyl, substituted cyclobutyl, cyclopentyl, substituted cyclopentyl, cyclohexyl, substituted cyclohexyl, cycloheptyl, substituted cycloheptyl, bicycloheptyl, bicyclooctyl, bicyclononyl, substituted bicycloalknyl, adamantyl, substituted adamantyl and the like. Substitutions are alkyl, aryl, $CF_3$, $CH_3$, $OCH_3$, OH, CN, COOR, COOH and the like.

In accordance with another aspect of the invention, there is disclosed a composition for use in the treatment of an allergic condition comprising the diacyl benzimidazole inhibitor of IgE disclosed above and at least one additional active ingredient, combined in a pharmaceutically acceptable diluent. The additional active ingredients may be selected from the group consisting of short-acting $\beta_2$-adrenergic agonists, like terbutaline and albuterol, long-acting $\beta_2$-adrenergic agonists, like salmeterol and formoterol, antihistamines, like loratadine, azelastine and ketotifen, phosphodiesterase inhibitors, anticholinergic agents, corticosteroids, inflammatory mediator release inhibitors and leukotriene receptor antagonists.

In accordance with another aspect of the invention, there is disclosed a family of diacyl benzimidazole compounds for use in the treatment of an allergic condition comprising the following species:

S-1

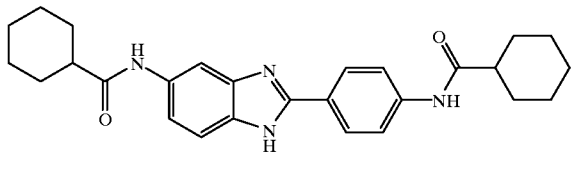

S-2

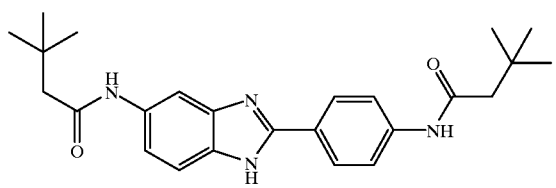

S-3

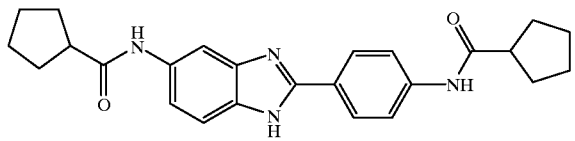

S-4

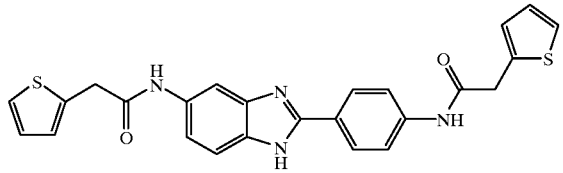

S-5

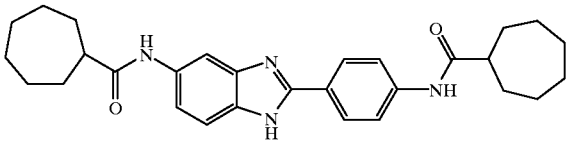

S-6

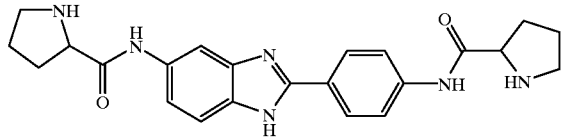

S-7

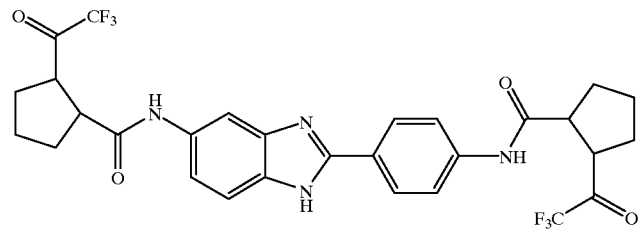

-continued
S-8
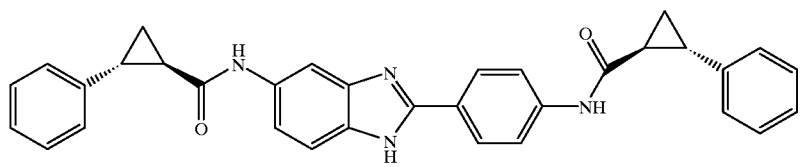
S-9
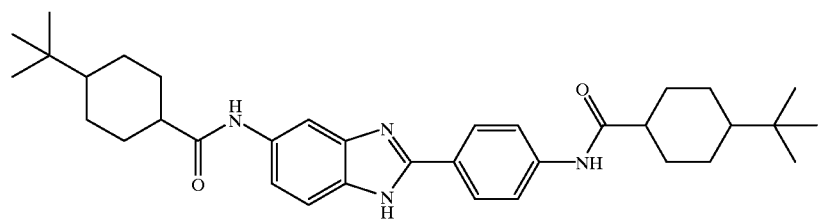
S-10
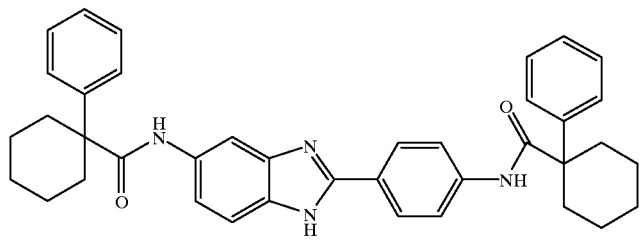
S-11
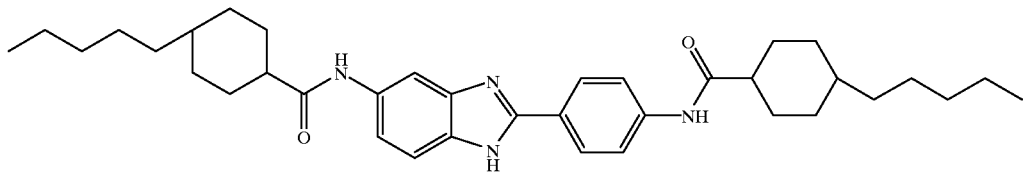
S-12
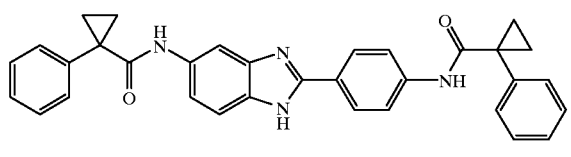
S-13
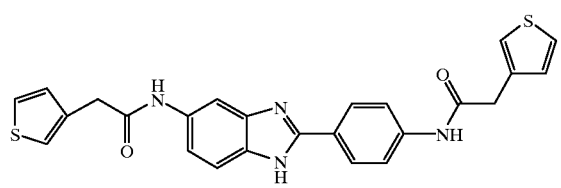
S-14
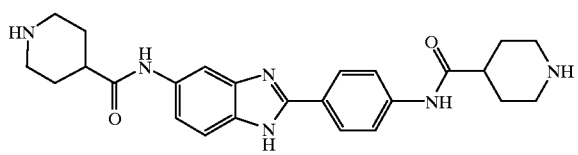
S-15
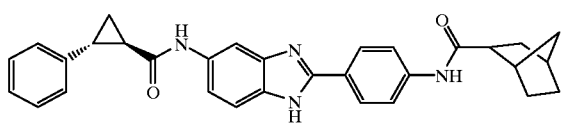
S-16
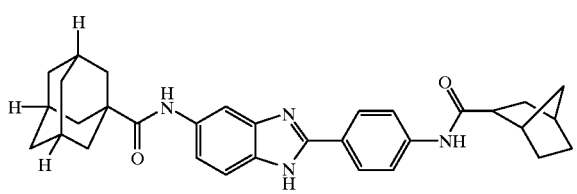
S-17
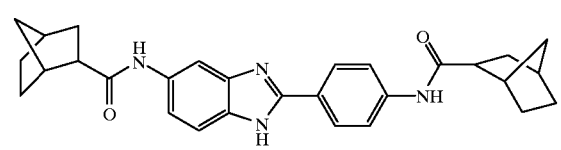

-continued
S-18
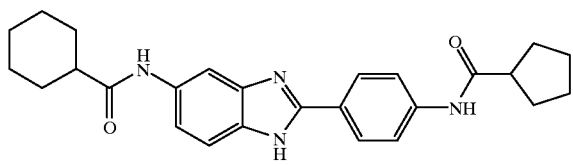
S-19
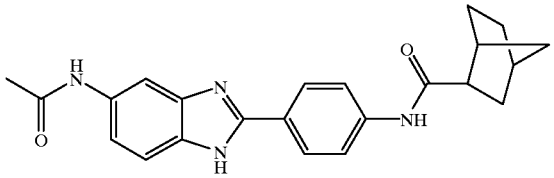
S-20
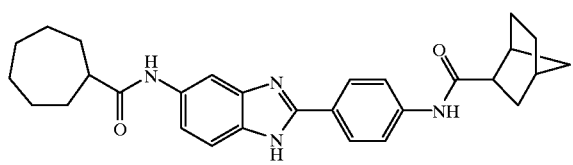
S-21
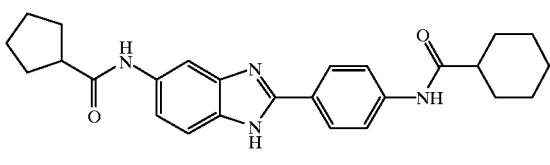
S-22
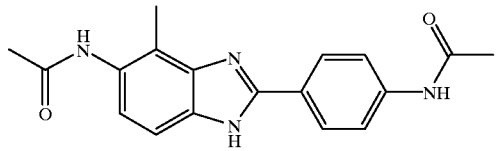
S-23
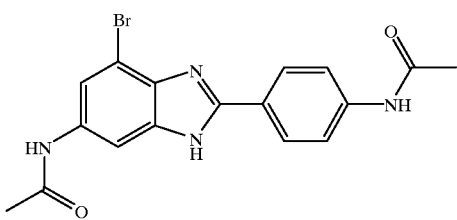
S-24
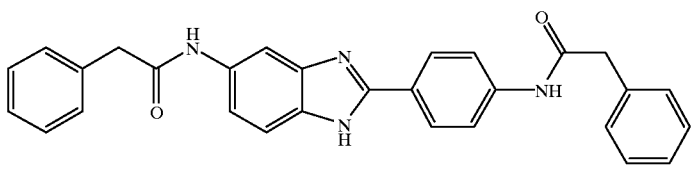
S-25
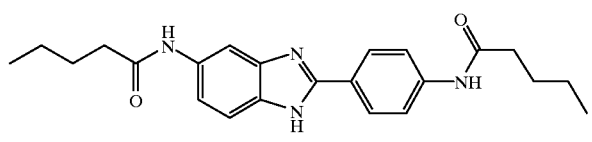
S-26
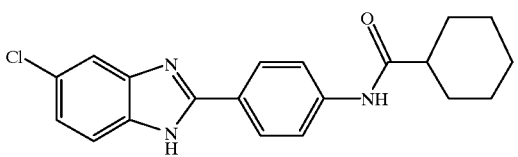
S-27
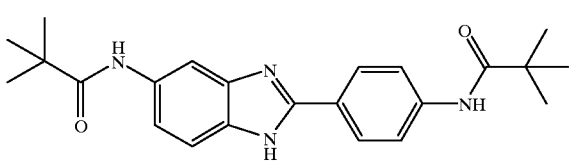
S-28
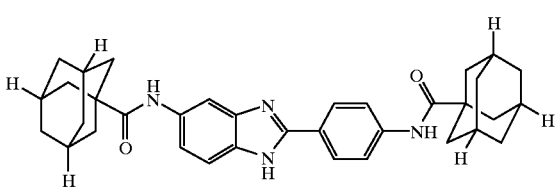
S-29
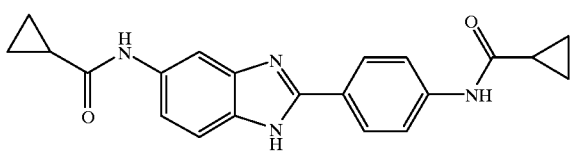
S-30
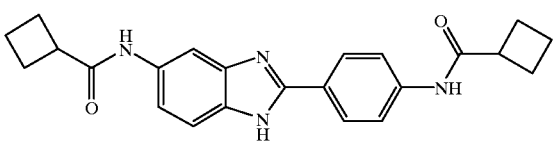

-continued
S-31
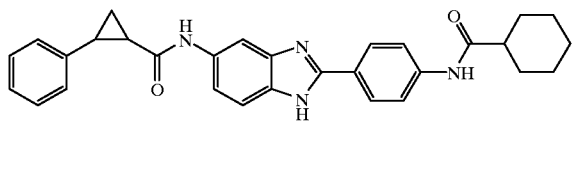
S-32
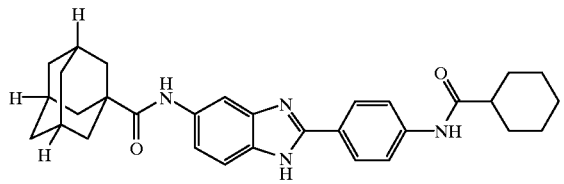
S-33
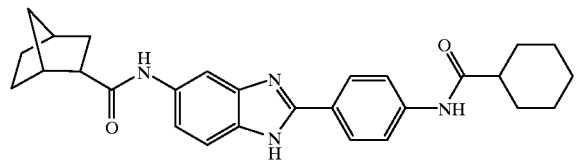
S-34
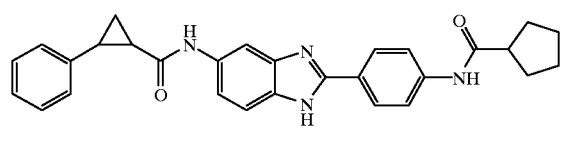
S-35
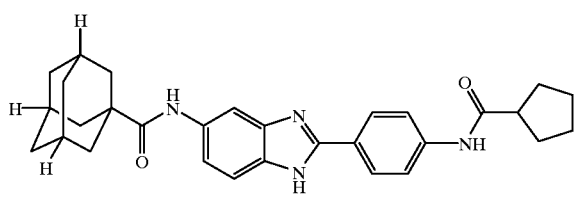
S-36
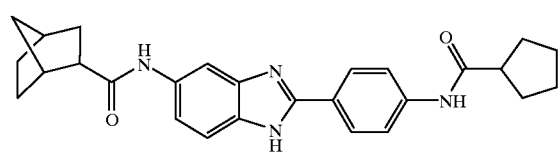
S-37
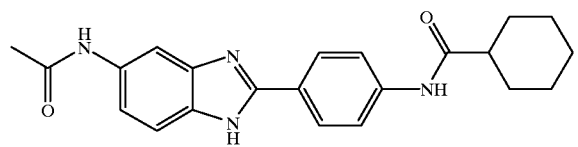
S-38
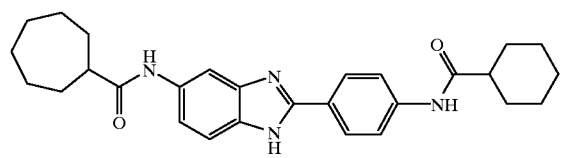
S-39
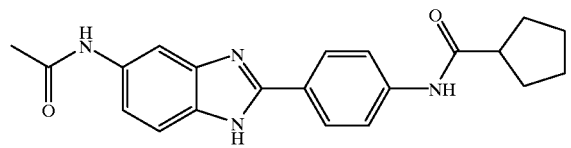
S-40
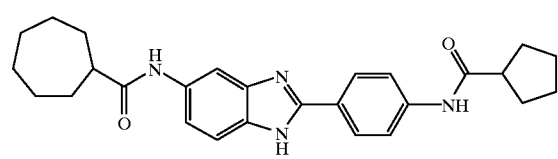
S-41
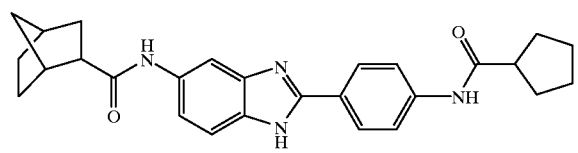
S-42
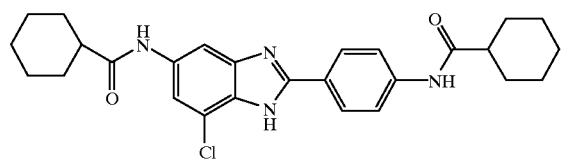
S-43
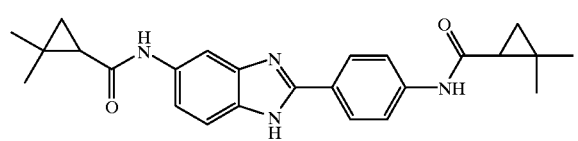
S-44
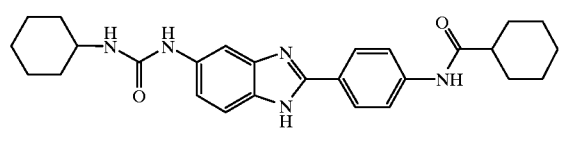

-continued
S-45
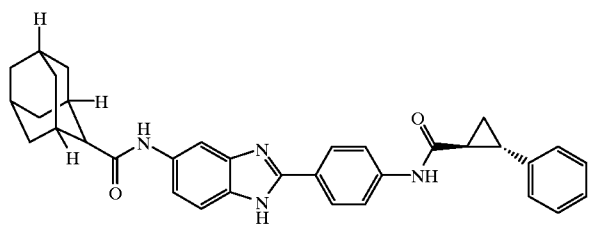
S-46
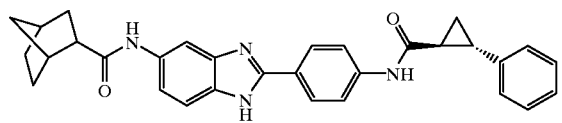
S-47
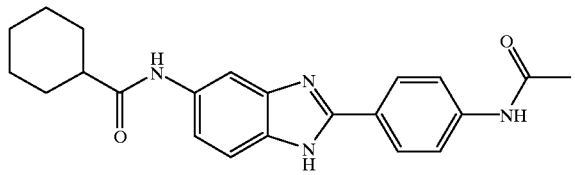
S-48
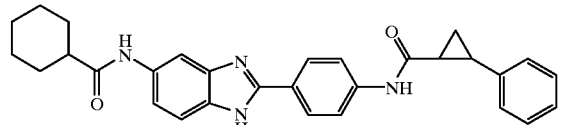
S-49
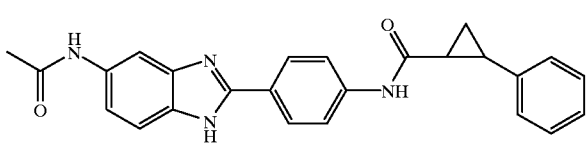
S-50
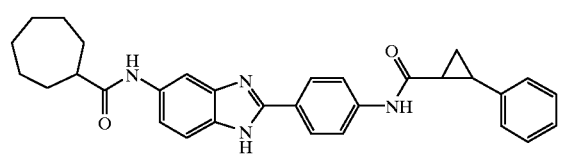
S-51
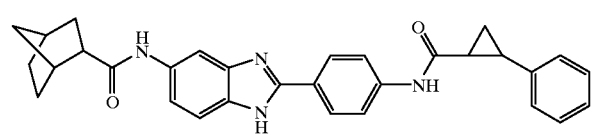
S-52
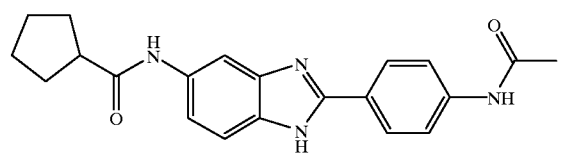
S-53
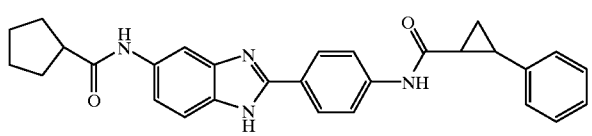
S-54
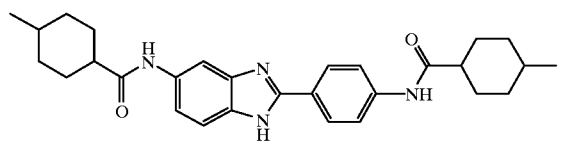
S-55
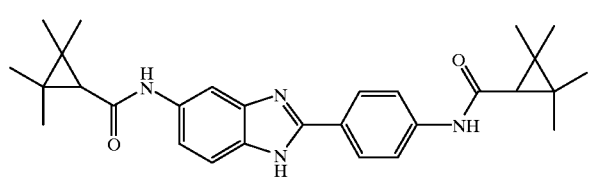
S-56
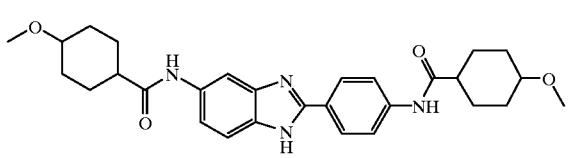
S-57
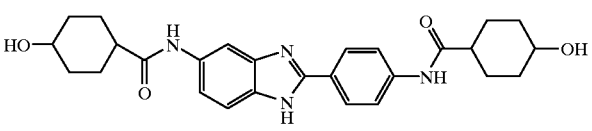
S-58
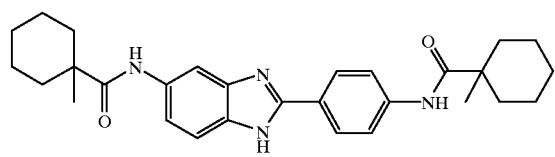
S-60
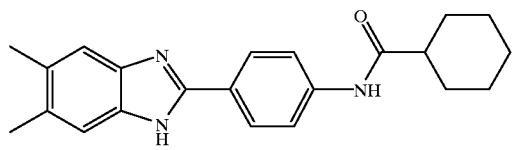
S-61
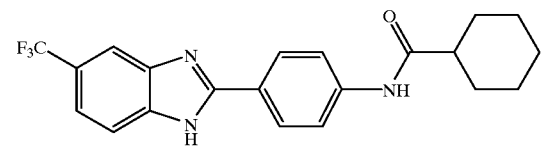

-continued
S-62
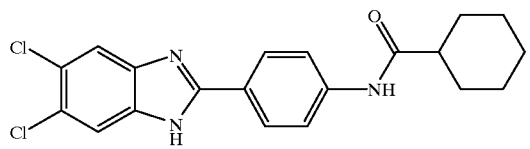
S-63
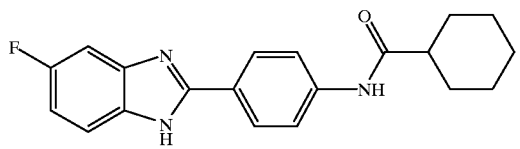
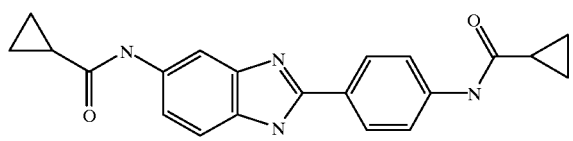
S-64
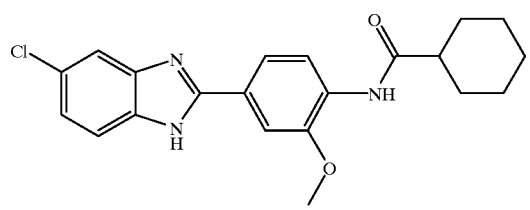
S-65
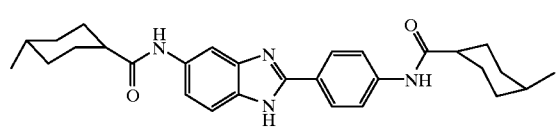
S-66
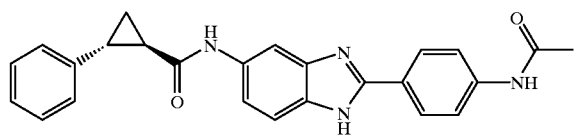
S-67
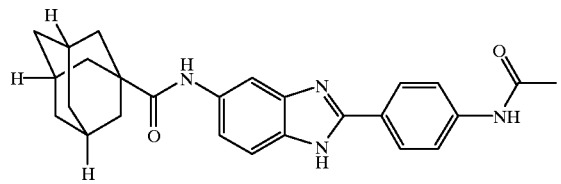
S-68
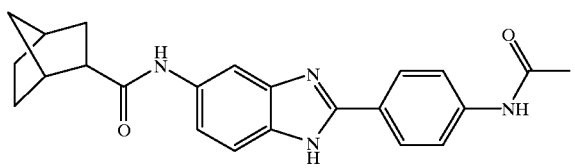
S-69
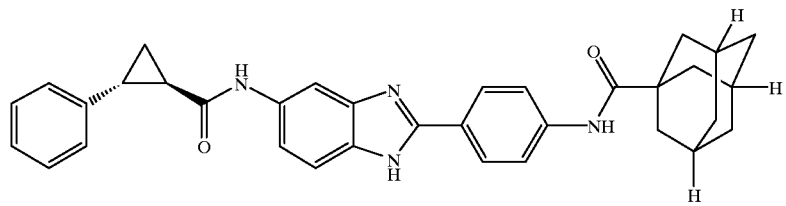
S-70
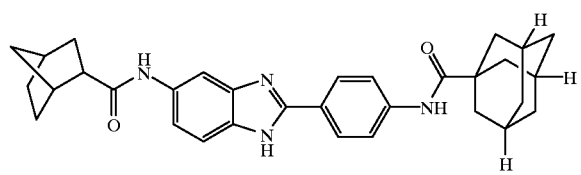
S-71
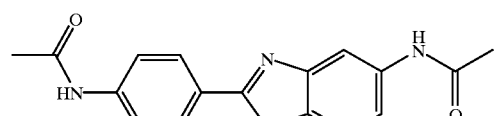

-continued
S-72
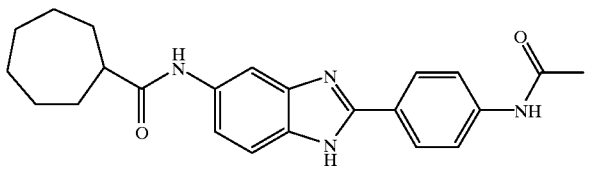
S-73
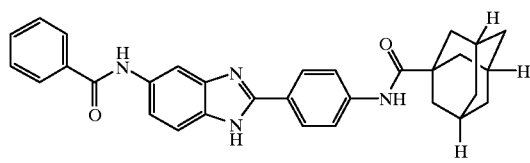
S-74
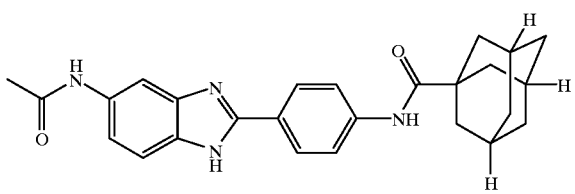
S-75
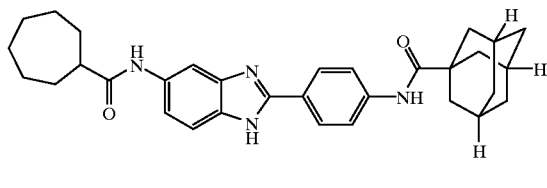
S-76
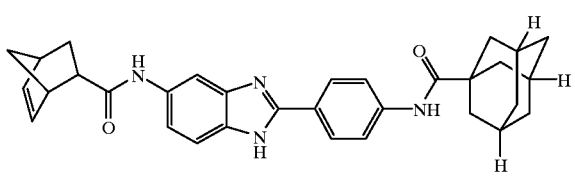
S-77
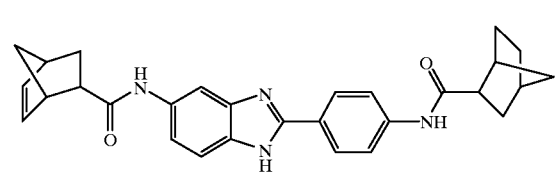
S-78
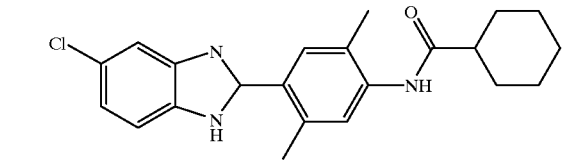
S-79
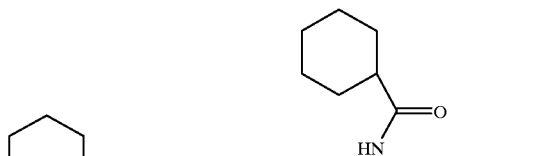
S-80
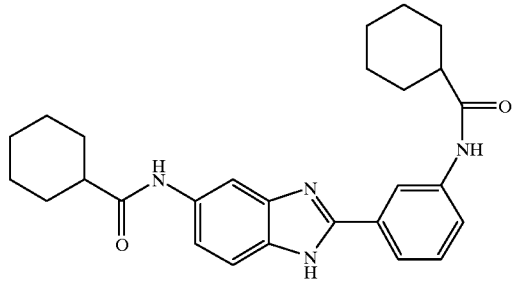
S-81
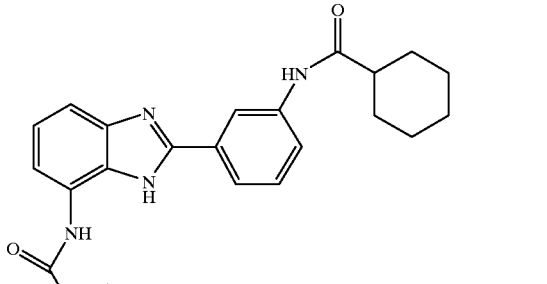
S-82
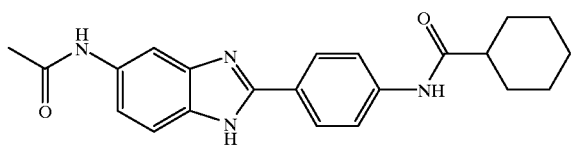
S-83
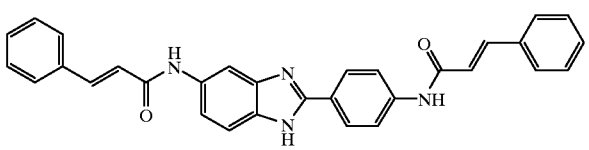

-continued
S-84
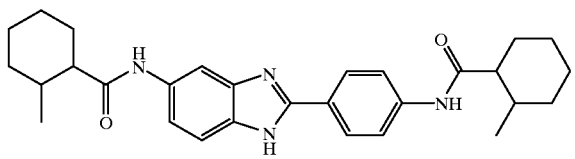
S-85
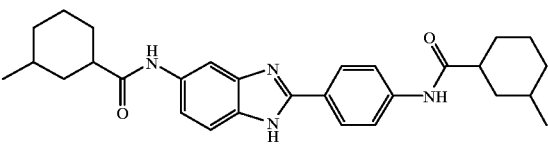
S-86
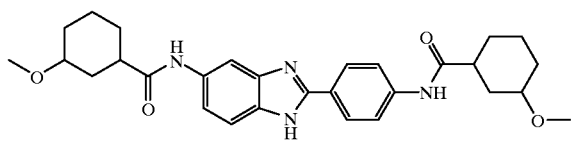
S-87
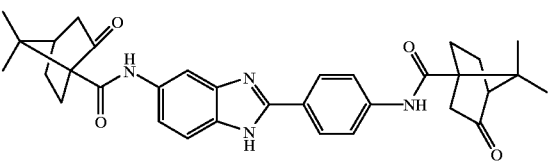
S-88
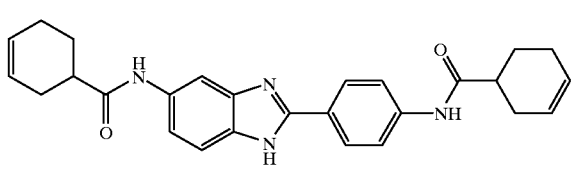
S-89
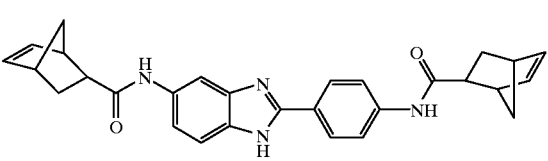
S-90
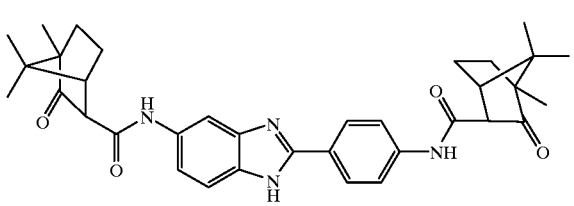
S-91
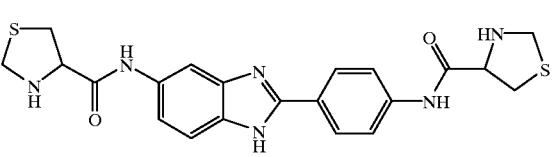
S-90
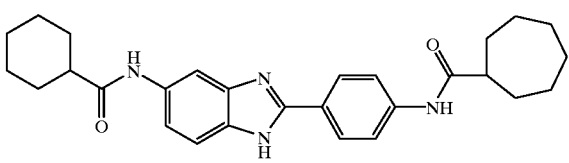
S-93
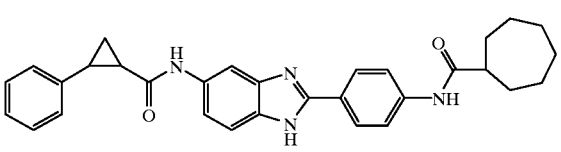
S-94
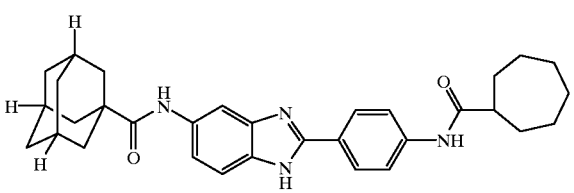
S-95
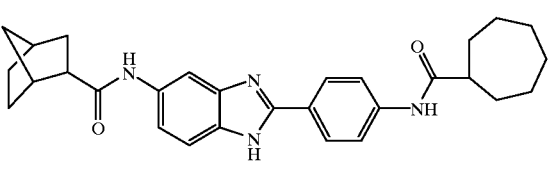
S-96
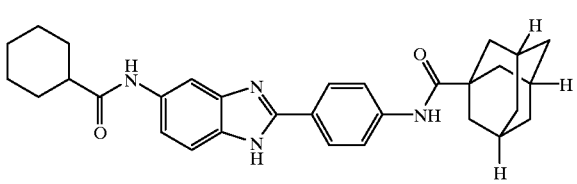
S-97
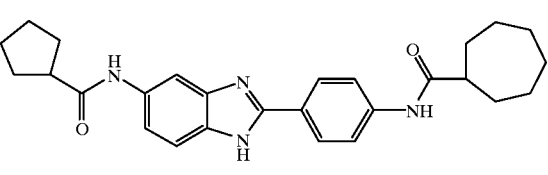

-continued
S-98
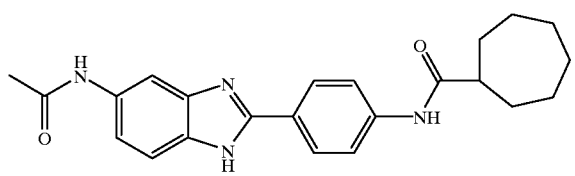
S-99
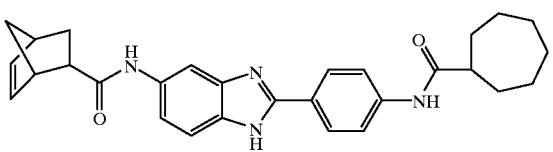
S-100
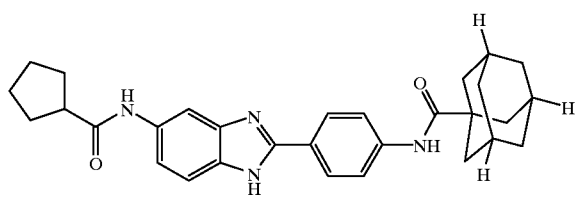
S-101
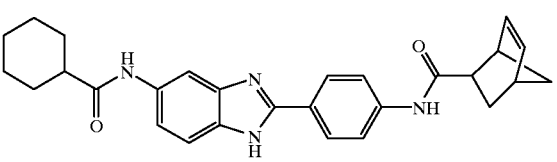
S-102
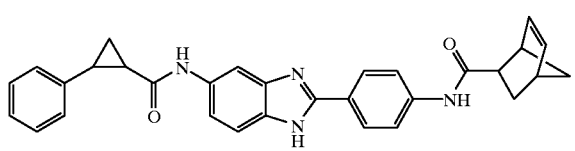
S-103
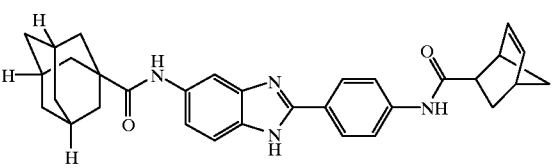
S-104
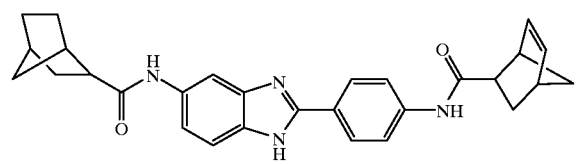
S-105
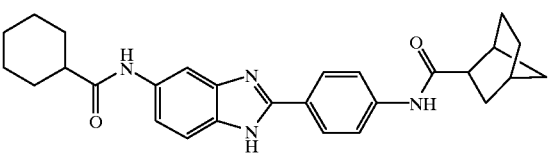
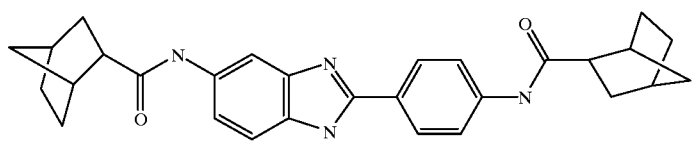
S-106
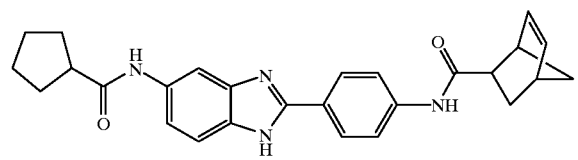
S-107
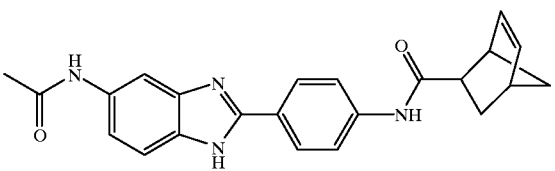
S-108
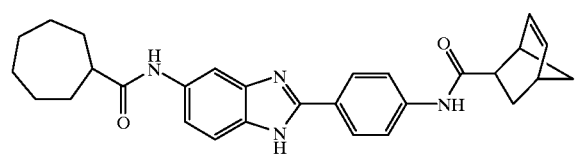
S-109
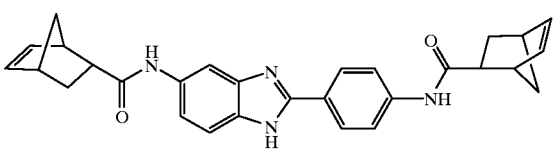
S-110
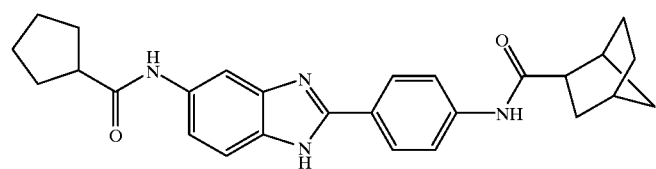

-continued
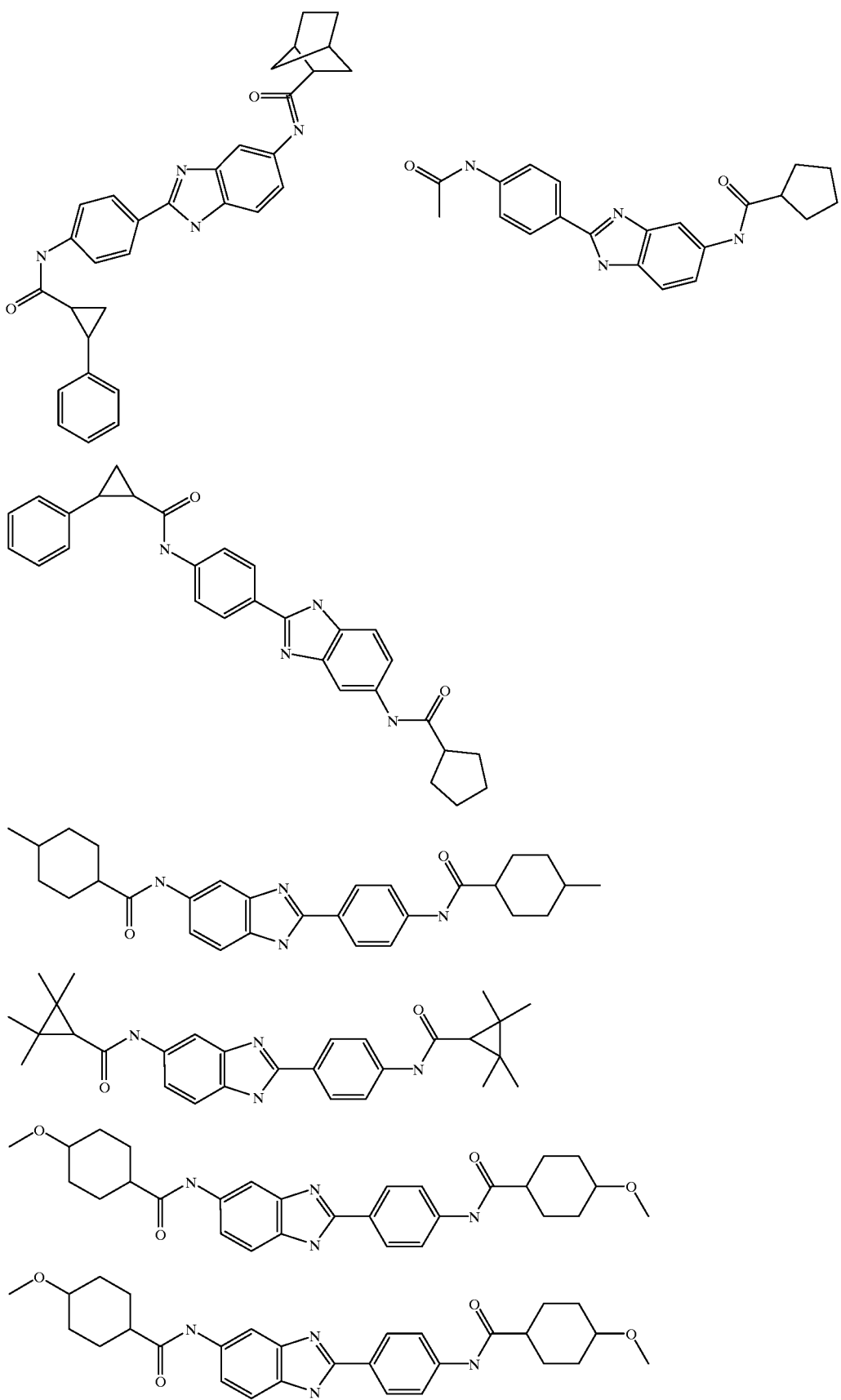

-continued
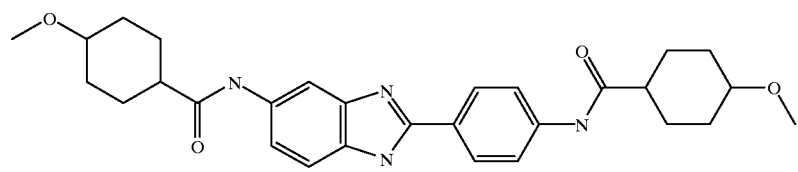
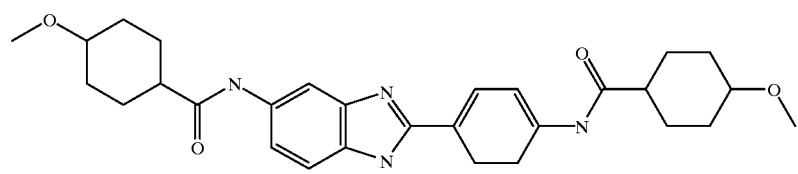
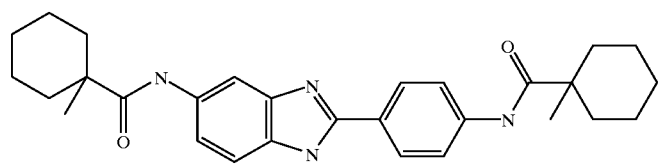
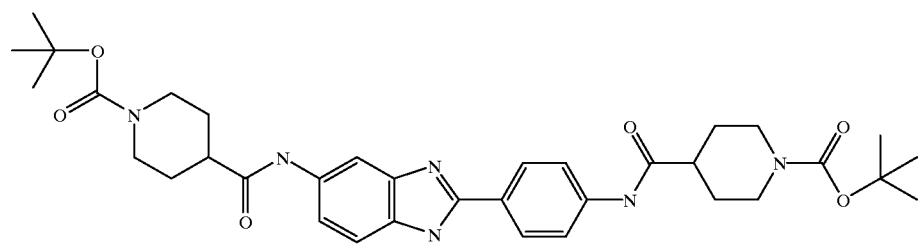
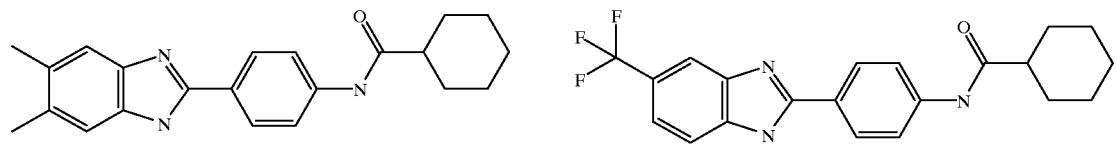
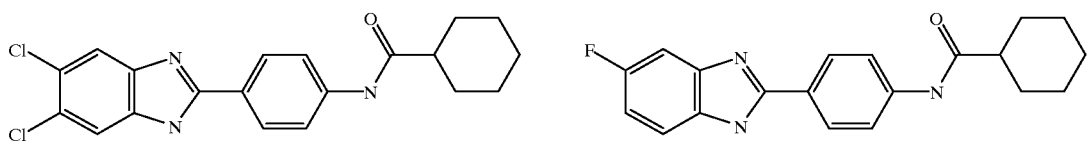
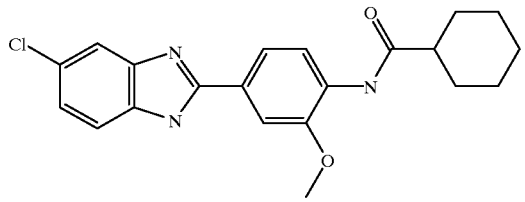
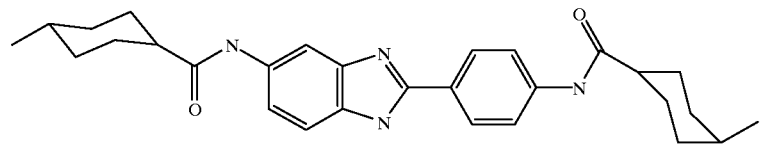
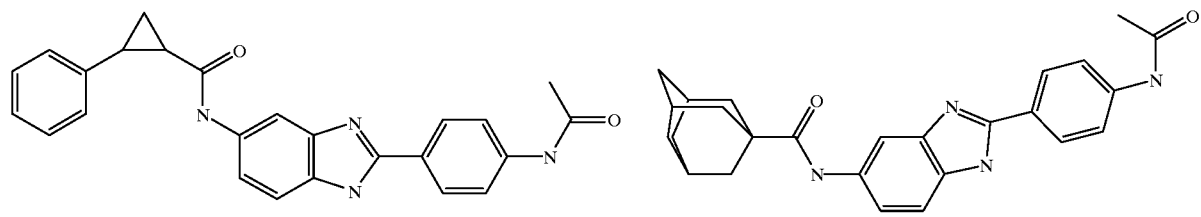

-continued
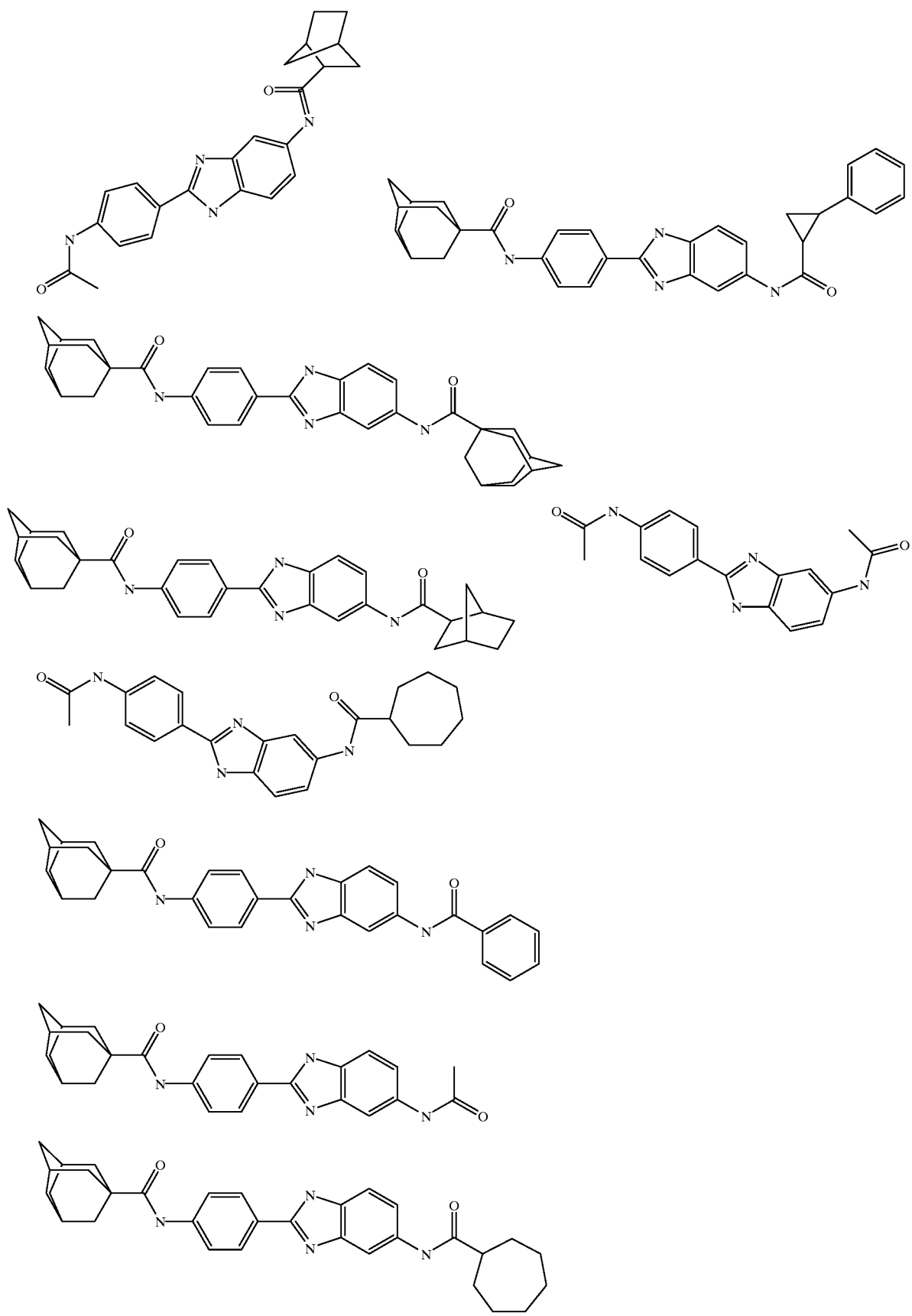

-continued
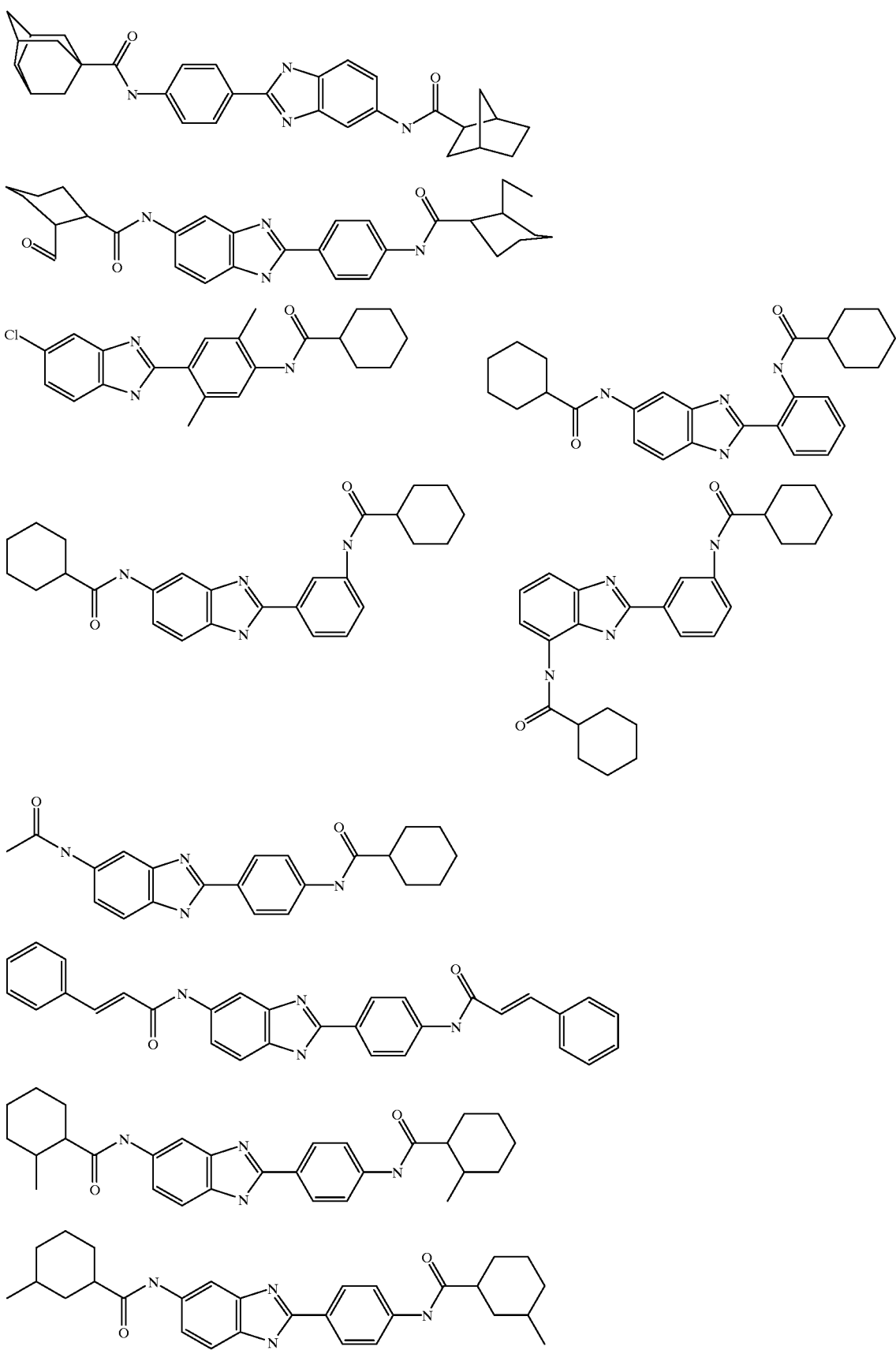

-continued
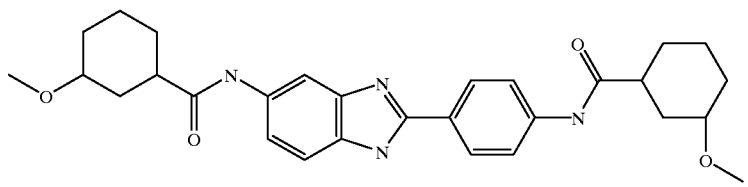
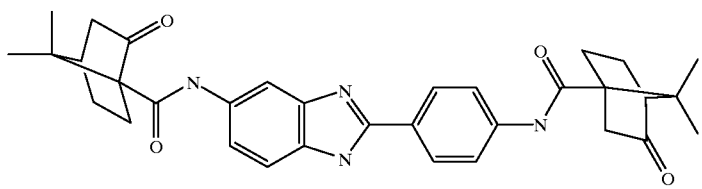
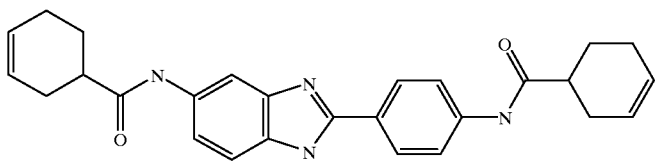
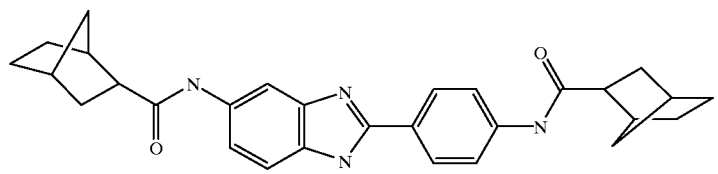
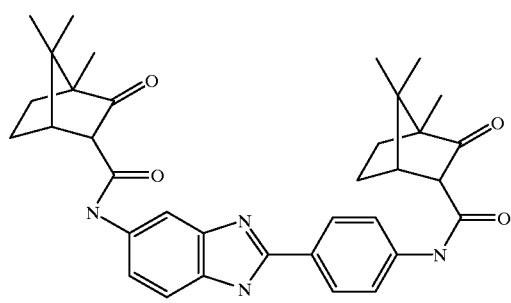
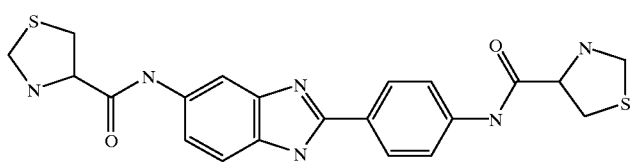
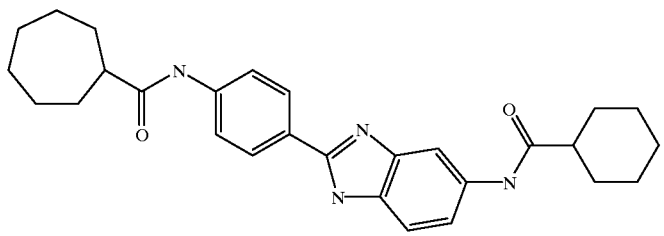
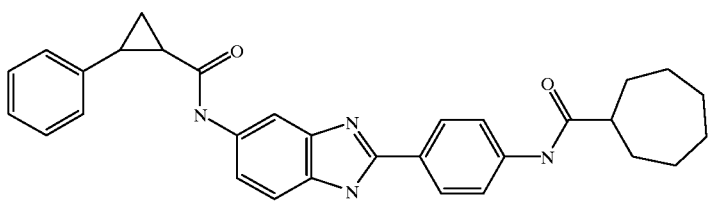

-continued
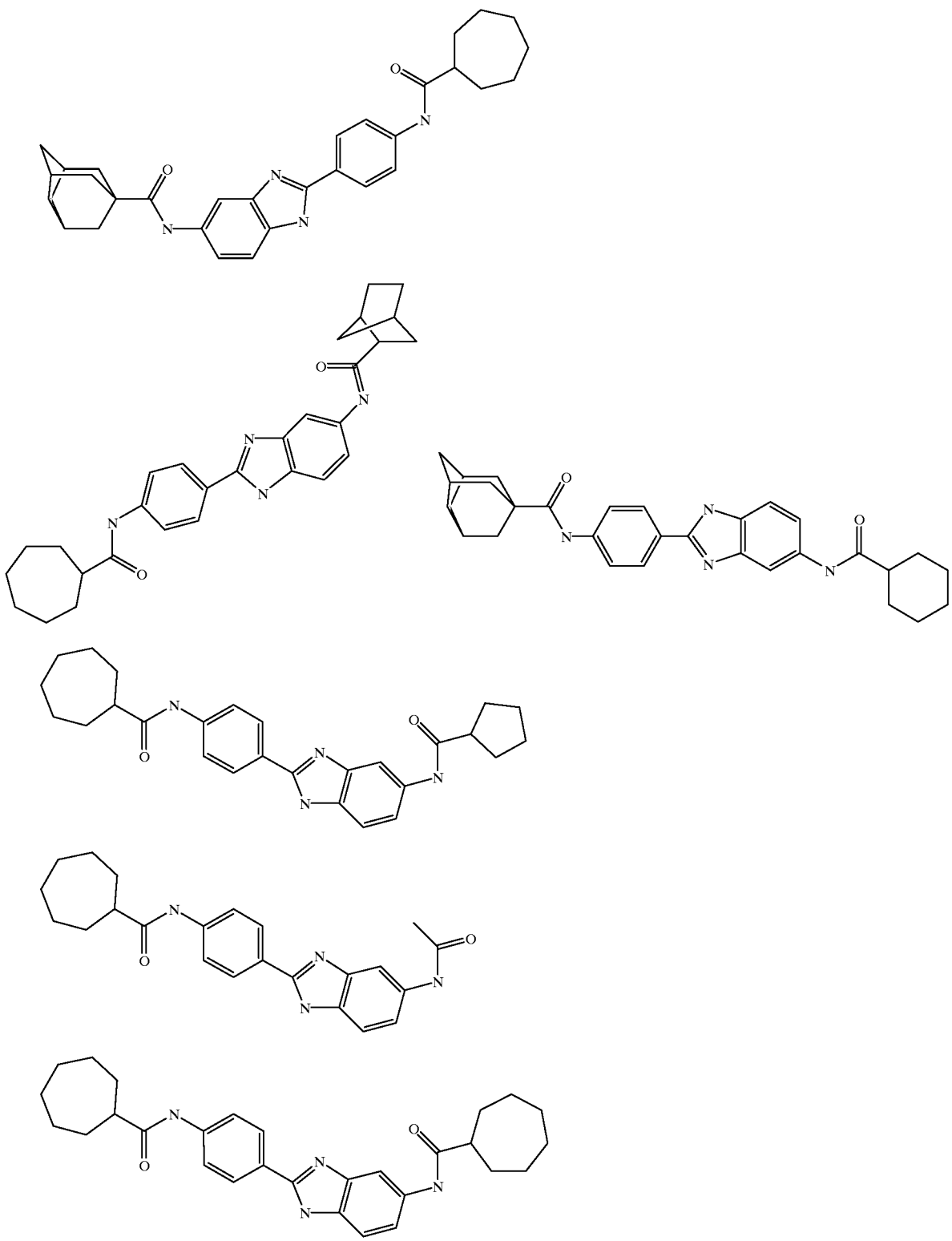

-continued
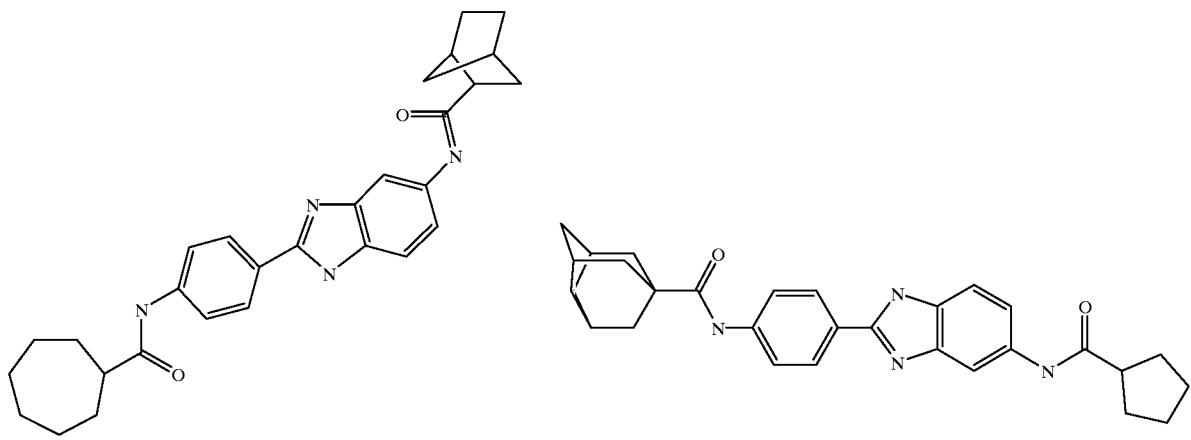
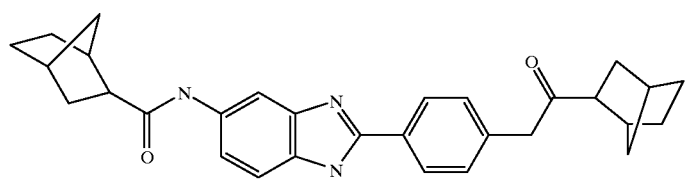
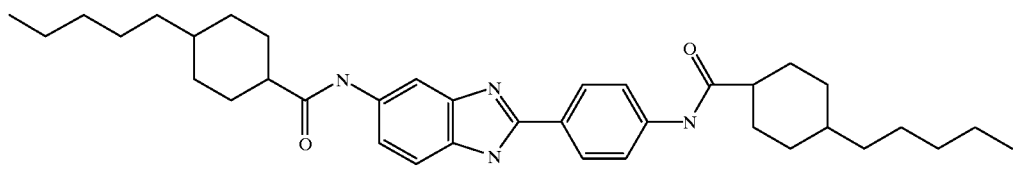
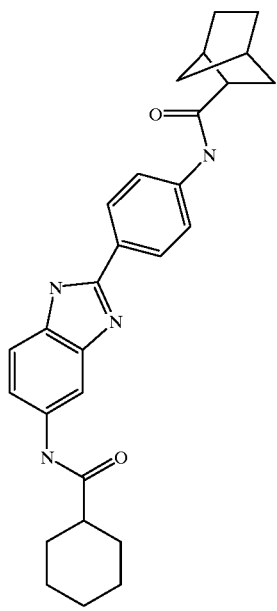
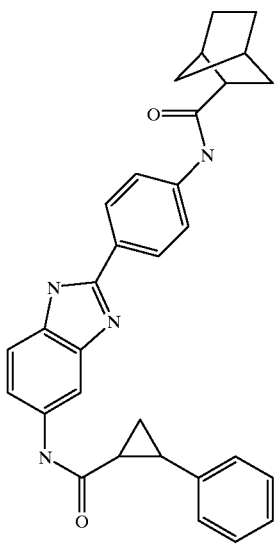

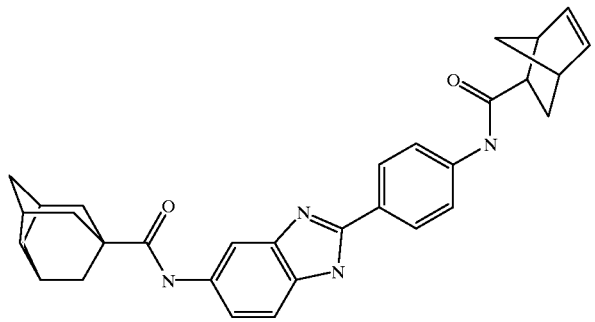
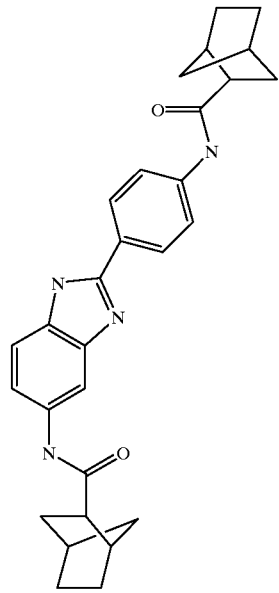
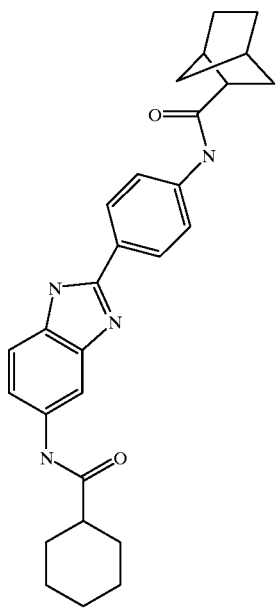
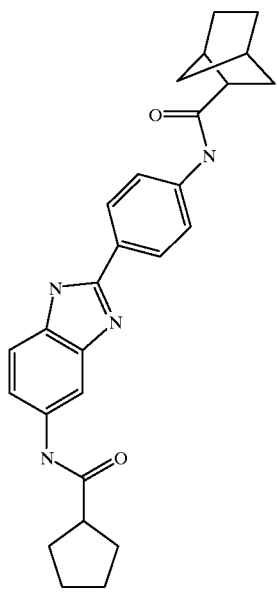
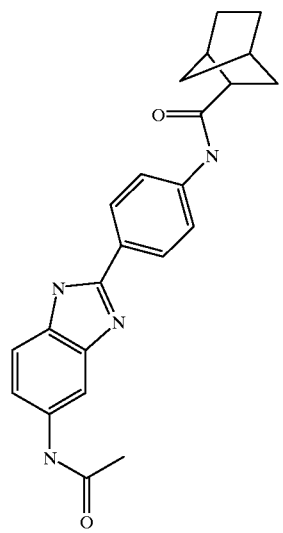

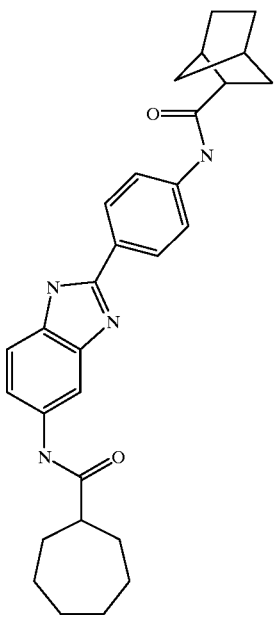 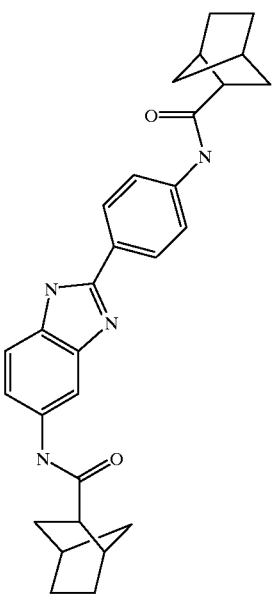 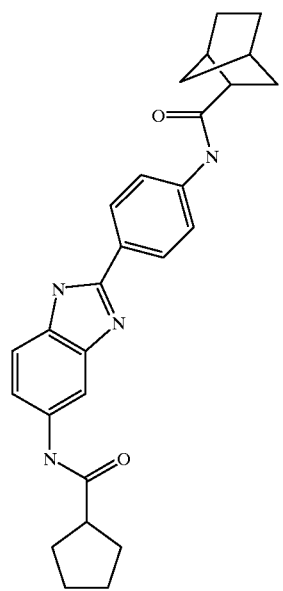
In accordance with another aspect of the present invention, there is disclosed a monoacylated variation of the disclosed genus. Several species of asymmetrical monoacyl benzimidazole compounds are disclosed. These species have the following formulas:
S-111
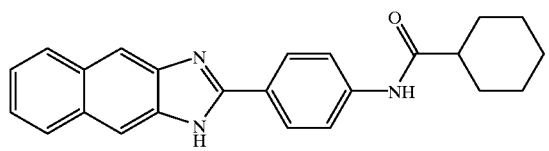
S-112
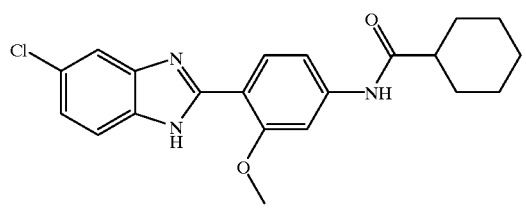
S-113
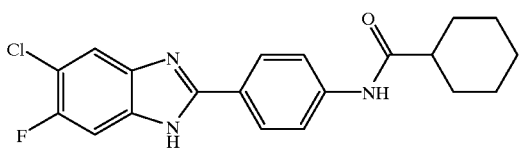
S-114
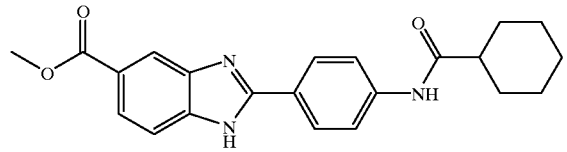
S-115
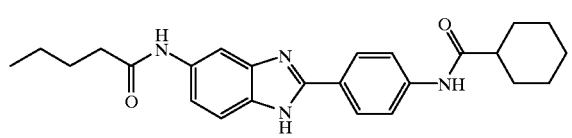
S-116
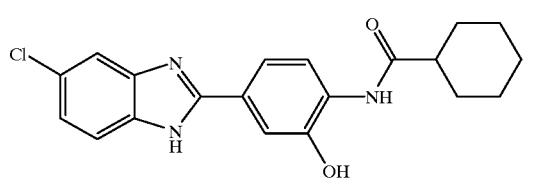
S-117
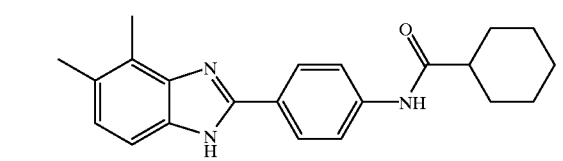
S-118
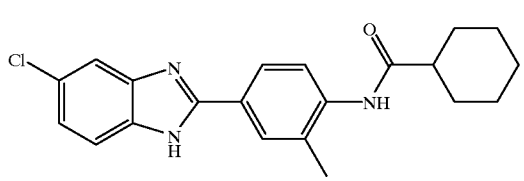

-continued

S-119
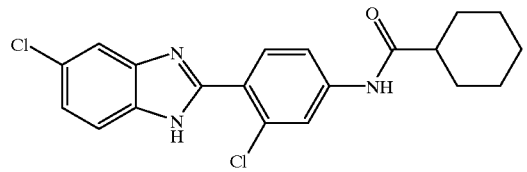

S-120
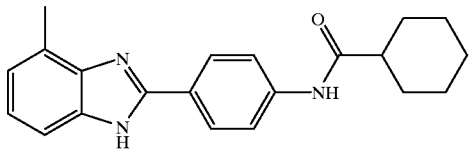

S-121
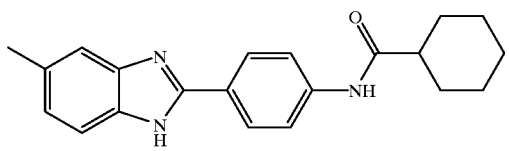

S-122
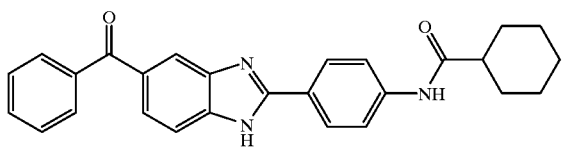

S-123
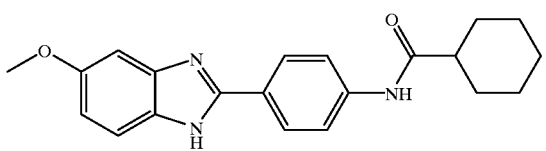

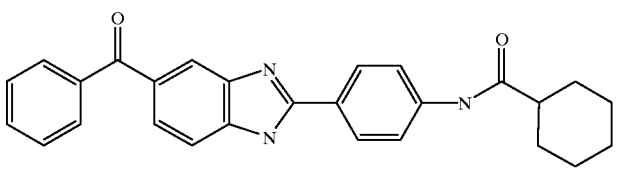

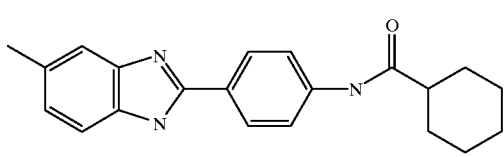

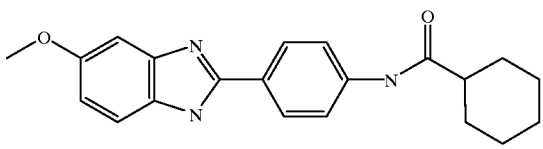

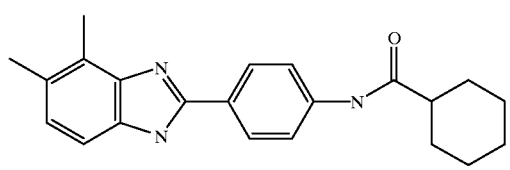

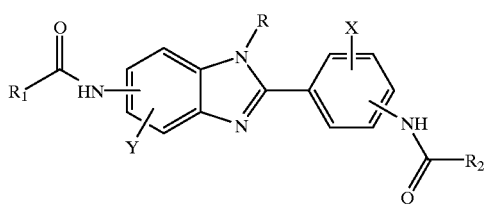

In accordance with another aspect of the present invention, there is disclosed a method for the preparation of a medicament for treatment of a condition associated with an excess IgE level. The compound has the formula:

X and Y are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$.

R is selected from the group consisting of H, $CH_3$, $C_2H_5$, $C_3H_7$, $C_4H_9$, $CH_2Ph$, and $CH_2C_6H_4$—F(p-).

$R_1$ and $R_2$ are independently selected from the group consisting of alkyl, cycloalkyl substituted cycloalkyl, multi-ring cycloalkyl, fused-ring aliphatic, cyclopropyl, substituted cyclopropyl, cyclobutyl, substituted cyclobutyl, cyclopentyl, substituted cyclopentyl, cyclohexyl, substituted cyclohexyl, cycloheptyl, substituted cycloheptyl, bicycloheptyl, bicyclooctyl, bicyclononyl, substituted bicycloalknyl, adamantyl, and substituted adamantyl, where the substitutions are selected from the group consisting of alkyl, aryl, $CF_3$, $CH_3$, $OCH_3$, OH, CN, COOR and COOH.

In accordance with another aspect of the present invention, there is disclosed a method of treating a mammal having a condition associated with an excess IgE level. The method comprises administering to the mammal an amount of a compound sufficient to reduced IgE levels in the mammal. The compound has the formula:

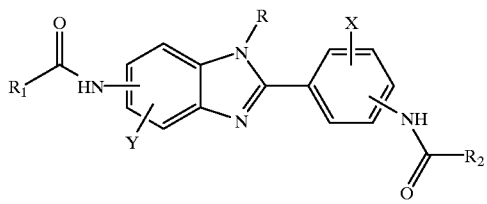

X and Y are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$.

R is selected from the group consisting of H, $CH_3$, $C_2H_5$, $C_3H_7$, $C_4H_9$, $CH_2Ph$, and $CH_2C_6H_4$—F(p-).

$R_1$ and $R_2$ are independently selected from the group consisting of alkyl, cycloalkyl substituted cycloalkyl, multi-ring cycloalkyl, fused-ring aliphatic, cyclopropyl, substituted cyclopropyl, cyclobutyl, substituted cyclobutyl, cyclopentyl, substituted cyclopentyl, cyclohexyl, substituted cyclohexyl, cycloheptyl, substituted cycloheptyl, bicycloheptyl, bicyclooctyl, bicyclononyl, substituted bicycloalknyl, adamantyl, and substituted adamantyl, where the substitutions are selected from the group consisting of alkyl, aryl, $CF_3$, $CH_3$, $OCH_3$, OH, CN, COOR and COOH.

In a variation of the above-disclosed method, at least one additional active ingredient may be administered in conjunction with the administration of the compound. The additional active ingredient may be combined with said compound in a pharmaceutically acceptable diluent and co-administered to the mammal. The additional active ingredient may be a short-acting $\beta_2$-adrenergic agonist selected from the group consisting of terbutaline and albuterol. In a variation, the additional active ingredient may be a long-acting $\beta_2$-adrenergic agonist selected from the group consisting of salmeterol and formoterol or an antihistamine selected from the group consisting of loratadine, azelastine and ketotifen. In another variation, the additional active ingredient may be a phosphodiesterase inhibitor, an anticholinergic agent, a corticosteroid, an inflammatory mediator release inhibitor or a leukotriene receptor antagonist.

The compound is preferably administered at a dose of about 0.01 mg to about 100 mg per kg body weight per day in divided doses of said compound for at least two consecutive days at regular periodic intervals.

Other variations within the scope of the present invention may be more fully understood with reference to the following detailed description.

DETAILED DESCRIPTION OF THE PREFERRED EMBODIMENT

The present invention is directed to small molecule inhibitors of IgE (synthesis and/or release) which are useful in the treatment of allergy and/or asthma or any diseases where IgE is pathogenic. The particular compounds disclosed herein were identified by their ability to suppress IgE levels in both ex vivo and in vivo assays. Development and optimization of clinical treatment regimens can be monitored by those of skill in the art by reference to the ex vivo and in vivo assays described below.

Ex-Vivo Assay

This assay begins with in vivo antigen priming and measures secondary antibody responses in vitro. The basic protocol was documented and optimized for a range of parameters including: antigen dose for priming and time span following priming, number of cells cultured in vitro, antigen concentrations for eliciting secondary IgE (and other Ig's) response in vitro, fetal bovine serum (FBS) batch that will permit optimal IgE response in vitro, the importance of primed CD4+ T cells and hapten-specific B cells, and specificity of the ELISA assay for IgE (Marcelletti and Katz, *Cellular Immunology* 135:471–489 (1991); incorporated herein by reference).

The actual protocol utilized for this project was adapted for a more high throughput analyses. BALB/cByj mice were immunized i.p. with 10 μg DNP-KLH adsorbed onto 4 mg alum and sacrificed after 15 days. Spleens were excised and homogenized in a tissue grinder, washed twice, and maintained in DMEM supplemented with 10% FBS, 100 U/ml penicillin, 100 μg/ml streptomycin and 0.0005% 2-mercaptoethanol. Spleen cell cultures were established (2–3 million cells/ml, 0.2 ml/well in quadruplicate, 96-well plates) in the presence or absence of DNP-KLH (10 ng/ml). Test compounds (2 μg/ml and 50 ng/ml) were added to the spleen cell cultures containing antigen and incubated at 37° C. for 8 days in an atmosphere of 10% $CO_2$.

Culture supernatants were collected after 8 days and Ig's were measured by a modification of the specific isotype-selective ELISA assay described by Marcelletti and Katz (Supra). The assay was modified to facilitate high throughput. ELISA plates were prepared by coating with DNP-KLH overnight. After blocking with bovine serum albumin (BSA), an aliquot of each culture supernatant was diluted (1:4 in phosphate buffered saline (PBS) with BSA, sodium azide and Tween 20), added to the ELISA plates, and incubated overnight in a humidified box at 4° C. IgE levels were quantitated following successive incubations with biotinylated-goat antimouse IgE (b-GAME), AP-streptavidin and substrate.

Antigen-specific IgG1 was measured similarly, except that culture supernatants were diluted 200-fold and biotinylated-goat antimouse IgG1 (b-GAMG1) was substituted for b-GAME. IgG2a was measured in ELISA plates that were coated with DNP-KLH following a 1:20 dilution of culture supernatants and incubation with biotinylated-goat antimouse IgG2a (b-GAMG2a). Quantitation of each isotype was determined by comparison to a standard curve. The level of detectability of all antibody was about 200–400 pg/ml and there was less than 0.001% cross-reactivity with any other Ig isotype in the ELISA for IgE.

In Vivo Assay

Compounds found to be active in the ex vivo assay (above) were further tested for their activity in suppressing IgE responses in vivo. Mice receiving low-dose radiation prior to immunization with a carrier exhibited an enhanced IgE response to sensitization with antigen 7 days later. Administration of the test compounds immediately prior to and after antigen sensitization, measured the ability of that drug to suppress the IgE response. The levels of IgE, IgG1 and IgG2a in serum were compared.

Female BALB/cByj mice were irradiated with 250 rads 7 hours after initiation of the daily light cycle. Two hours later, the mice were immunized i.p. with 2 μg of KLH in 4 mg alum. Two to seven consecutive days of drug injections were initiated 6 days later on either a once or twice daily basis. Typically, i.p. injections and oral gavages were administered as suspensions (150 μl/injection) in saline with 10% ethanol and 0.25% methylcellulose. Each treatment group was composed of 5–6 mice. On the second day of drug administration, 2 μg of DNP-KLH was administered i.p. in 4 mg alum, immediately following the morning injection of drug. Mice were bled 7–21 days following DNP-KLH challenge.

Antigen-specific IgE, IgG1 and IgG2a antibodies were measured by ELISA Periorbital bleeds were centrifuged at 14,000 rpm for 10 min, the supernatants were diluted 5-fold in saline, and centrifuged again. Antibody concentrations of each bleed were determined by ELISA of four dilutions (in triplicate) and compared to a standard curve: anti-DNP IgE (1:100 to 1:800), anti-DNP IgG2a (1:100 to 1:800), and anti-DNP IgG1 (1:1600 to 1:12800).

Diacyl Benzimidazole Inhibitors of IgE

Several species embraced by the following generic formula were synthesized and evaluated for their effectiveness in down-regulating IgE in the ex vivo and in vivo assays.

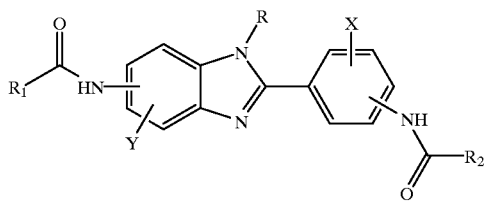

X and Y are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$.

R is selected from the group consisting of H, $CH_3$, $C_2H_5$, $C_3H_7$, $C_4H_9$, $CH_2Ph$, and $CH_2C_6H_4$—F(p-).

$R_1$ and $R_2$ are independently selected from tie group consisting of alkyl, cycloalkyl substituted cycloalkyl, multi-ring cycloalkyl, fused-ring aliphatic, cyclopropyl, substituted cyclopropyl, cyclobutyl, substituted cyclobutyl, cyclopentyl, substituted cyclopentyl, cyclohexyl, substituted cyclohexyl, cycloheptyl, substituted cycloheptyl, bicycloheptyl, bicyclooctyl, bicyclononyl, substituted bicycloalknyl, adamantyl, substituted adamantyl and the like. Substitutions are alkyl, aryl, $CF_3$, $CH_3$, $OCH_3$, OH, CN, COOR, COOH and the like.

Another related genus is the monoacylated variation illustrated below:

S-124

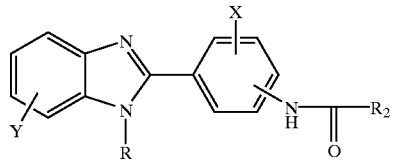

X is selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$. Y is selected from the group consisting of mono, di, and tri substituted H, alkyl, alkoxy, aryl, substituted aryl, hydroxy, halogen, amino, alkylamino, nitro, cyano, $CF_3$, $OCF_3$, $CONH_2$, CONHR and $NHCOR_1$.

R is selected from the group consisting of H, $CH_3$, $C_2H_5$, $C_3H_7$, $C_4H_9$, $CH_2Ph$, and $CH_2C_6H_4$—F(p).

$R_1$ is selected from the group consisting of alkyl, cycloalkyl substituted cycloalkyl, multi-ring cycloalkyl, fused-ring aliphatic, cyclopropyl, substituted cyclopropyl, cyclobutyl, substituted cyclobutyl, cyclopentyl, substituted cyclopentyl, cyclohexyl, substituted cyclohexyl, cycloheptyl, substituted cycloheptyl, bicycloheptyl, bicyclooctyl, bicyclononyl, substituted bicycloalknyl, adamantyl, substituted adamantyl and the like. Substitutions are alkyl, aryl, $CF_3$, $CH_3$, $OCH_3$, OH, CN, COOR, COOH and the like.

Synthesis of the Combinatorial Library

The diacyl benzimidazole compounds of the present invention were prepared using the following synthesis reactions, wherein the desired acid chlorides are selected from the R1 and R2 groups provided in the Table.

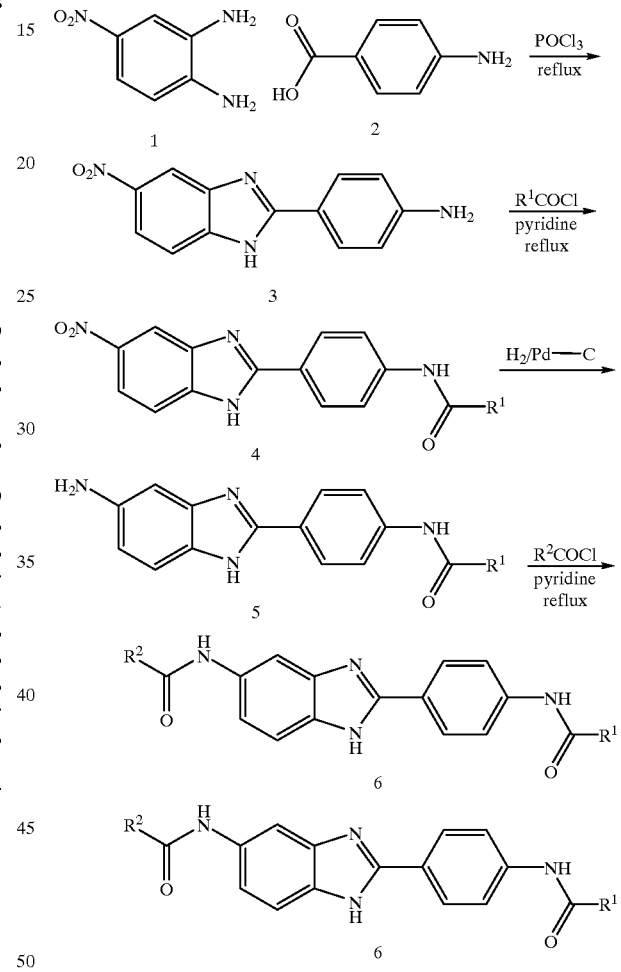

Synthesis of 3

4-Nitro-1,2-phenylenediamine (10 g, 65.3 mmol) and 4-aminobenzoic acid (8.95 g, 65.3 mmol) were taken in a round bottomed flask and phosphorus oxychloride (95 ml) was added slowly. The reaction mixture was allowed to stir under reflux conditions. After 18 h, the reaction was allowed to cool and then poured slowly into an ice water mixture in an Erlenmeyer flask with vigorous stirring. Greenish yellow precipitate fell out which was then filtered and washed with copious amounts of water. The residue was then dried to obtain 16.9 g of crude desired product. Mass spectrum analysis (positive ion) indicated presence of 3.

Synthesis of 4

Benzimidazole 3 (800 mg, 3.14 mmol) was dissolved in dry pyridine (5 ml) in a scintillation vial and the desired acid chlorides (1.1 eq) were added slowly. The reactions were carried out in an oven at 60° C. After 16 h, the reaction was cooled to RT and DI water was added. Precipitation took place, which was filtered off, washed with water and air dried. The aqueous layer was extracted with EtOAc (6×50 ml), dried over anhydrous Na$_2$SO$_4$ and the solvent was removed in vacuo to result in a colored solid. By positive ion MS the desired monoacylated product was found to be present in the initial precipitate as well as in the organic layer. Hence the solid residues obtained were combined and used as such for the reduction step.

Reduction of 4

Crude monoacylated nitro benzimidazole 4 (1.22 g, 3.40 mmol) was dissolved in MeOH (20 ml) and minimum amount of THF was added for complete dissolution to occur. Catalytic amount of 10% Pd on C was added and the solution was degassed and allowed to stir at 3.4 atm pressure under H$_2$ atmosphere for 4 h. Upon completion of reaction as observed via TLC, the reaction mixture was filtered through celite and the solvent was removed under reduced pressure to afford 979 mg of crude residue.

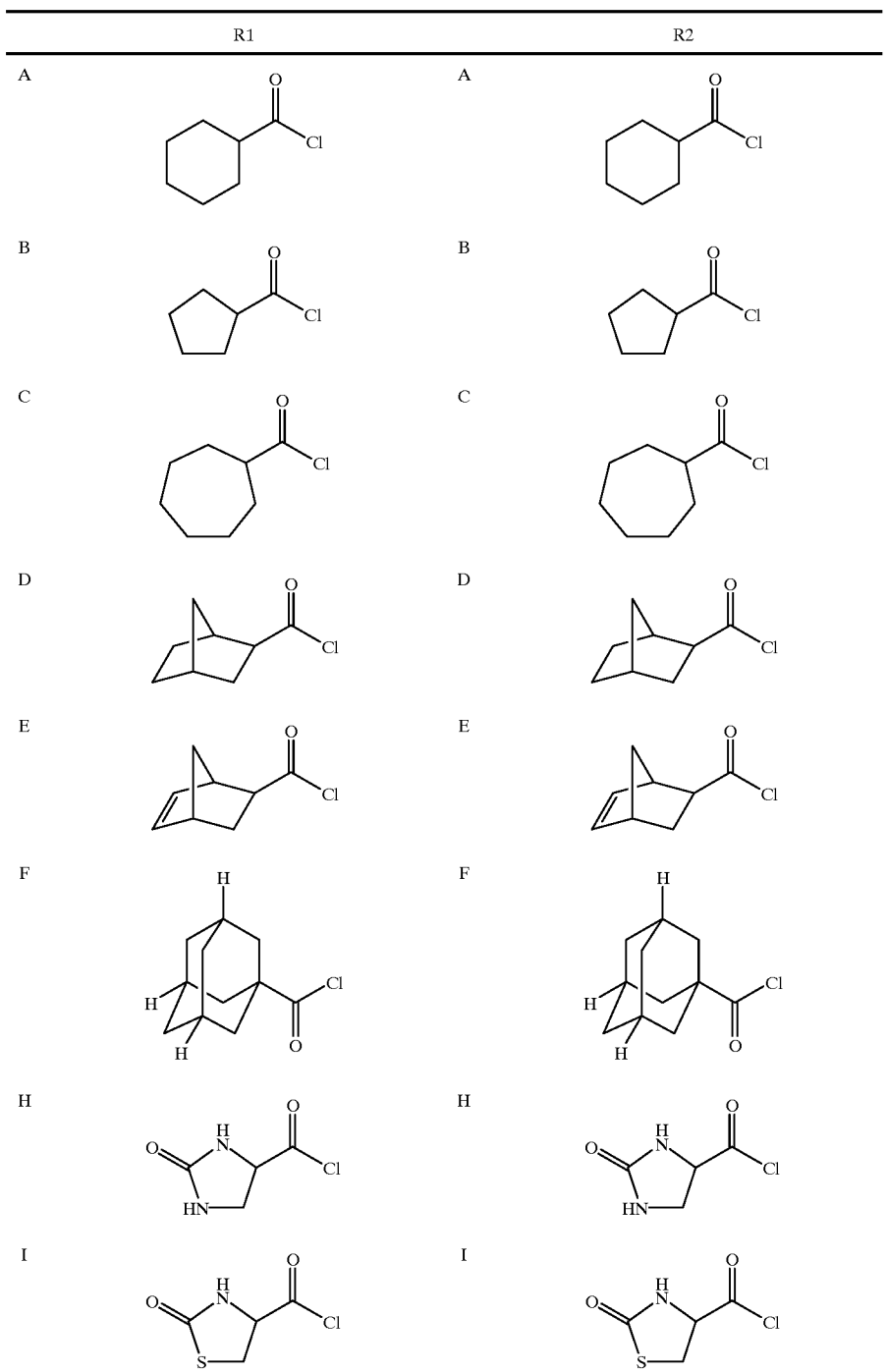

-continued

| | R1 | | R2 |
|---|---|---|---|
| J | (camphor-derived acid chloride) | J | (camphor-derived acid chloride) |
| K | 2-methylcyclohexanecarbonyl chloride | K | 2-methylcyclohexanecarbonyl chloride |
| L | 3-methylcyclohexanecarbonyl chloride | L | 3-methylcyclohexanecarbonyl chloride |
| M | 3-methoxycyclohexanecarbonyl chloride | M | 3-methoxycyclohexanecarbonyl chloride |
| N | (norbornyl methyl ketone) | N | (norbornyl methyl ketone) |
| O | (camphor methyl ketone) | O | (camphor methyl ketone) |
| P | 4-(trifluoromethyl)cyclohexanecarbonyl chloride | P | 4-(trifluoromethyl)cyclohexanecarbonyl chloride |
| Q | 1-methylcyclohexanecarbonyl chloride | Q | 1-methylcyclohexanecarbonyl chloride |
| R | 4-methoxycyclohexanecarbonyl chloride | R | 4-methoxycyclohexanecarbonyl chloride |

-continued

| R1 | R2 |
|---|---|
| S 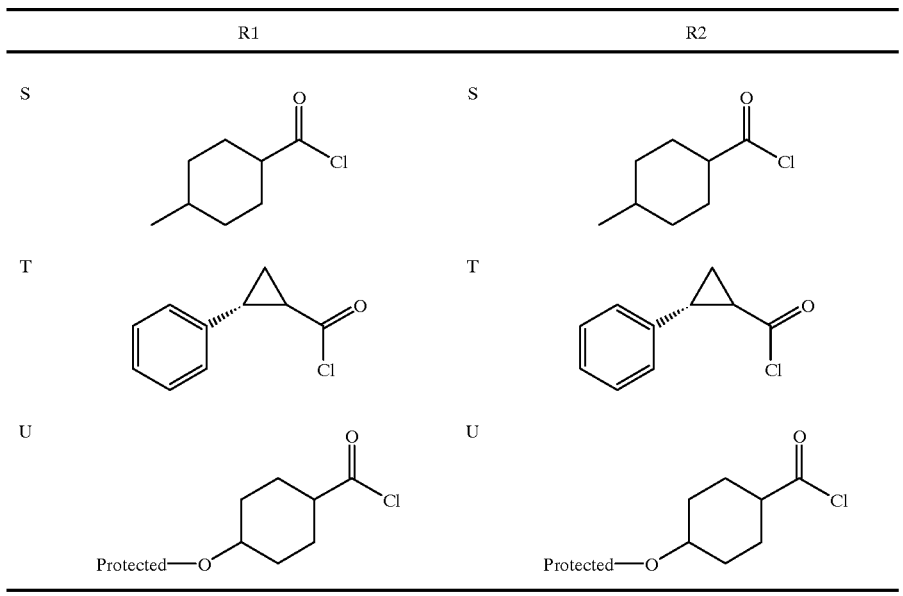 | S |
| T | T |
| U | U |

General Organic Analyses

HPLC/MS data was obtained using a Gilson semi-prep HPLC with a Gilson 170 Diode Array UV detector and PE Sciex API 100LC MS based detector. A Waters 600E with a Waters 490E UV detector was also used for recording HPLC data. The compounds were eluted with a gradient of $CH_3CN$ (with 0.0035% TFA) and $H_2O$ (with 0.01% TFA). Both HPLC instruments used Advantage C18 60A 5µ 50 mm×4.6 mm columns from Thomson Instrument Company. Mass spectra were obtained by direct injection and electrospray ionization on a PE Sciex API 100LC MS based detector. Thin layer chromatography was performed using Merck 60F-254 aluminum backed precoated plates. Flash chromatography was carried out on Merck silica gel 60 (230–400 mesh) purchased from EM Scientific.

Syntheses of Symmetrical Diamides

The symmetrical diacyl benzimidazole compounds of the present invention were generally prepared from 2-(4-aminophenyl)-5-aminobenzimidazole, which was obtained by reduction of 2-(4-nitrophenyl)-6-nitrobenzimidazole.

S-125

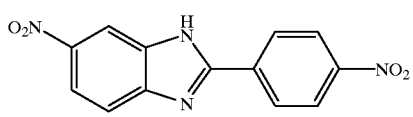

2-(4-nitrophenyl)-6-nitrobenzimidazole

The dinitro benzimidazole was prepared as follows: a mixture of 4-nitrophenylenediamine (6.4 g, 41.83 mmol) and 4-nitrobenzoic acid (7.86 g, 47 mmol) was dissolved in $POCl_3$ (250 ml) and heated to reflux for 2 h. The reaction mixture was cooled, poured on to ice, and stirred for 30 min. The resulting solid was filtered and washed with methanol and sodium bicarbonate to remove unreacted acid and allowed to dry overnight to give the desired product as a brown solid (5.8 g). The product was characterized by electrospray mass spectroscopy (mp>300° C.).

2-(4-Aminophenyl)-5-aminobenzimidazole was prepared by suspending the above solid (75 g) in THF (75 ml), to which was added Pd-C (10% Pd by weight). The flask was purged with hydrogen and stirred under a balloon of hydrogen overnight. TLC and MS showed starting material was still present so the reaction was allowed to continue over the weekend. TLC indicated complete reaction, the reaction was filtered through celite and washed with methanol. The solvent was removed under reduced pressure to give a dark brown solid (0.37 g) that was used without further purification.

S-126

2-(4-aminophenyl)-5-aminobenzimidazole

Alternatively, the 2-(4-aminophenyl)-5-aminobenzimidazole was prepared by the following reduction: 2-(4-nitrophenyl)-6-nitrobenzimidazole (8.9 g, 31 mmole) was suspended in concentrated HCl (100 ml) to which was added stannous chloride (42.3 g 180 mmole). The reaction mixture was heated to reflux for 5 hrs. The mixture was cooled to RT and the HCl salt of the desired product was precipitated by the addition of ethanol. The resulting solid was filtered, re-dissolved in water and the solution made basic by the addition of concentrated ammonium hydroxide. The resulting precipitate was filtered and dried overnight under vacuum to yield the desired product as a gray solid (6.023 g, 26.9 mmole, 87%). The product characterized by electrospray mass spectroscopy and HPLC (mp. 222–227° C.).

2-(4-Aminophenyl)-5-methoxy benzimidazole was synthesized from 2-(4-nitrophenyl)-5-methoxy benzimidazole, which was prepared as follows: 1,2-diamino-4-methoxybenzene (1.26 g, 10.0 mmole was mixed with 4-nitrobenzoic acid (1.67 g, 9.8 mmole) and dissolved in $POCl_3$ (10 ml) and heated to reflux for 2.5 hours. The reaction mixture was cooled and cautiously poured onto ice.

The resulting solid was filtered, washed with NaHCO₃ and used without further purification.

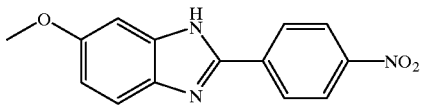

2-(4-nitrophenyl)-5-methoxy benzimidazole

S-127

2-(4-Aminophenyl)-5-methoxy benzimidazole was prepared by dissolving 1.0 g of the above nitrobenzimidazole in 30% Na₂S.9H₂O (20 ml) with stirring at RT for 21 h. The reaction mixture was diluted with water and extracted with EtOAc. The combined organic extracts were dried over sodium sulfate and concentrated under vacuum. The product was characterized by mass spectroscopy.

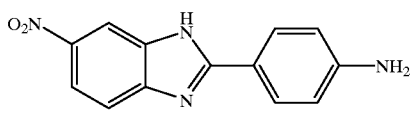

2-(4-aminophenyl)-5-methoxy benzimidazole

S-128

2-(4-Aminophenyl)-5,6-dichloro benzimidazole was synthesized from 2-(4-nitrophenyl)-5,6-dichloro benzimidazole, which was prepared as follows: 1,2-diamino-4,5-dichlorobenzene (1.68 g, 10.0 mmole) was mixed with 4-nitrobenzoic acid (1.58 g, 9.3 mmole), dissolved in POCl₃ (10 ml), and heated to reflux for 2.5 hours. The reaction mixture was cooled and cautiously poured onto ice. The resulting solid was filtered, washed with NaHCO₃ and used without further purification.

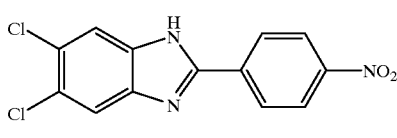

2-(4-nitrophenyl)-5,6-dichloro benzimidazole

S-129

2-(4-Aminophenyl)-5,6-dichloro benzimidazole was prepared by dissolving 1.0 g of the above nitrobenzimidazole in 30% Na₂S.9H₂O (20 ml) with stirring at RT for 21 h. The reaction mixture was diluted with water and extracted with EtOAc. The combined organic extracts were dried over sodium sulfate and concentrated under vacuum. The product was characterized by mass spectroscopy.

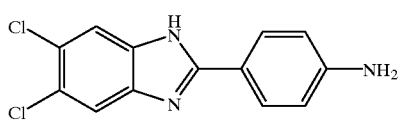

2-(4-Aminophenyl)-5,6-dichloro benzimidazole

S-130

2-(4-aminophenyl)-7-methyl benzimidazole was synthesized from 2-(4-nitrophenyl)-7-methyl benzimidazole, which was prepared by mixing 1,2-diamino-3-methylbenzene (1.24 g, 10.0 mmole) with 4-nitrobenzoic acid (1.69 g, 9.8 mmole), dissolved in POCl₃ (10 ml), and heated to reflux for 2.5 hours. The reaction mixture was cooled and cautiously poured onto ice. The resulting solid was filtered, washed with NaHCO₃ and used without further purification.

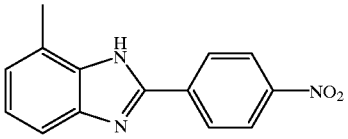

2-(4-nitrophenyl)-7-methyl benzimidazole

S-131

2-(4-Aminophenyl)-7-methyl benzimidazole was synthesized by dissolving 1.0 g of the above nitrobenzimidazole in 30% Na₂S.9H₂O (20 ml) with stirring at RT for 4.5 h. The reaction mixture was diluted with water and extracted with EtOAc. The combined organic extracts were dried over sodium sulfate and concentrated under vacuum. The product was characterized by mass spectroscopy.

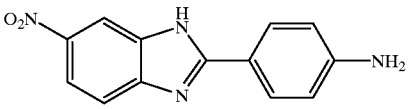

2-(4-aminophenyl)-7-methylbenzimidazole

S-132

2-(4-Aminophenyl)-6-methyl benzimidazole was synthesized from 2-(4-nitrophenyl)-6-methyl benzimidazole, which was prepared by mixing 1,2-diamino-4-methylbenzene (1.24 g, 9.8 mmole) with 4-nitrobenzoic acid (1.6 g, 9.9 mmole) and dissolved in POCl₃ (10 ml) and heated to reflux for 2.5 hours. The reaction mixture was cooled and cautiously poured onto ice. The resulting solid was filtered, washed with NaHCO₃ and used without further purification.

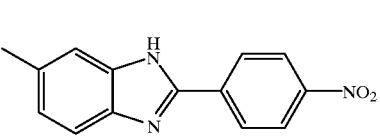

2-(4-nitrophenyl)-6-methylbenzimidazole

S-133

2-(4-Aminophenyl)-6-methyl benzimidazole was synthesized by dissolving 1.0 g of the above nitrobenzimidazole in 30% Na₂S.9H₂O (20 ml) with stirring at RT for 4.5 h. The reaction mixture was diluted with water and extracted with EtOAc. The combined organic extracts were dried over sodium sulfate and concentrated under vacuum. The product was characterized by mass spectroscopy.

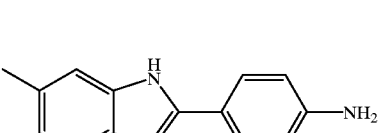

2-(4-aminophenyl)-6-methylbenzimidazole

S-134

2-(4-Aminophenyl)-5,6-dimethyl benzimidazole was synthesized from 2-(4-nitrophenyl)-5,6-dimethyl benzimidazole, which was prepared by mixing 1,2-diamino-4,5-dimethylbenzene (1.38 g, 10.1 mmole) with 4-nitrobenzoic acid (1.69 g, 9.9 mmole) and dissolved in POCl₃ (10 ml) and heated to reflux for 2.5 hours. The reaction mixture was cooled and cautiously poured onto ice. The resulting solid was filtered, washed with NaHCO₃ and used without further purification.

S-135

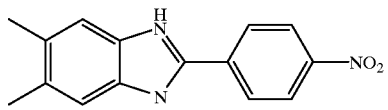

2-(4-nitrophenyl)-5,6-dimethylbenzimidazole 2-(4-Aminophenyl)-5,6-dimethyl benzimidazole was synthesized by dissolving 1.0 g of the above nitrobenzimidazole (31.1) in 30% Na₂S.9H₂O (20 ml) with stirring at RT for 4.5 h. The reaction mixture was diluted with water and extracted with EtOAc. The combined organic extracts were dried over sodium sulfate and concentrated under vacuum. The product was characterized by mass spectroscopy.

S-136

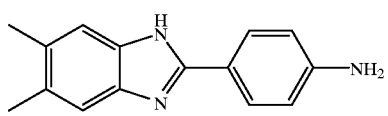

2-(4-aminophenyl)-5,6-dimethylbenzimidazole

The subsequent preparation of symmetrical diamides was accomplished by one of the following methods:

Method A 2-(4-Aminophenyl)-6-aminobenzimidazole (1 mmole) was suspended in THF (5 ml) to which was added DIEA (2.5 mmole) and mixture cooled to −78° C. To the above cooled mixture was added the acid chloride (2.5 mmole) and let warm to RT overnight. Water (2 ml) is added to the reaction and extracted with EtOAc. The combined organic extracts were combined washed with NaHCO₃ (aq.) and concentrated under reduced pressure. The resulting residue was purified on silica gel (hexanes/EtOAc or MeOH/CH₂Cl₂) or reverse phase HPLC (CH₃CN/H₂O).

Method B 2-(4-Aminophenyl)-6-aminobenzimidazole (1 mmole) and DMAP (cat.) was dissolved in pyridine (5 ml). To the above solution was added the acid chloride (2.5 mmole) and the reaction stirred overnight at 60° C. The reaction was cooled to room temperature and water added to precipitate the product. The resulting solid was collected by filtration with the solid being washed by hexanes and water and NaHCO₃ (aq.). The resulting residue was purified on silica gel (hexanes/EtOAc or MeOH/CH₂Cl₂) or reverse phase HPLC (CH₃CN/H₂O).

Method C 2-(4-Aminophenyl)-6-aminobenzimidazole (1.0 mmole) was suspended in THF (10 ml) to which was added K₂CO₃ (2.5 mmole) in water (0.5 ml). and mixture cooled to −78° C. To the above cooled mixture was added the acid chloride (2.5 mmole) and let warm to RT overnight. Water (10 ml) was added to the reaction and extracted with EtOAc. The combined organic extracts were combined washed with NaHCO₃ (aq.) and concentrated under reduced pressure. The resulting residue was purified on silica gel (hexanes/EtOAc or MeOH/CH₂Cl₂) or reverse phase HPLC (CH₃CN/H₂O).

Method D

The carboxylic acid (2.2 mmole), EDC (2.2 mmole) and DMAP (cat.) was dissolved in hot pyridine. To the above solution was added 2-(4-aminophenyl)-6-aminobenzimidazole (1.0 mmole) and heated to 60° C. overnight. The cooled reaction mixture was partitioned between water and EtOAc. The organic layer was washed with NaHCO₃, dried over Na₂SO₄ and concentrated under vacuum. The resulting residue was purified on silica gel (hexanes/EtOAc or MeOH/CH₂Cl₂) or reverse phase HPLC (CH₃CN/H₂O).

Diacyl Benzimidazole Species

The following species encompassed within the disclosed generic formula were synthesized and tested for their ability to suppress IgE. The species are numbered below.

(1) 2-(N-Cyclohexylcarbanoyl-4'-aminophenyl)-6-(cyclohexylcarbanoylamino)-benzimidazole was prepared by Method A from 2-(4-aminophenyl)-6-aminobenzimidazole (0.195 g, 0.87 mmole) and cyclohexylcarbonyl chloride (0.291 ml, 0.319 g, 2.175 mmole). The resulting solid (76.7 mg) was purified by preparative HPLC.

S-1

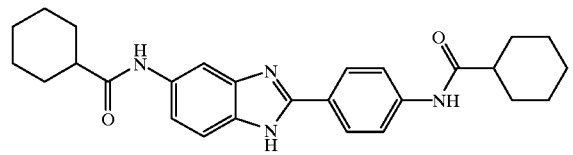

(1)

(2) Bis-t-butylacetyl benzimidazole was prepared by Method A from 2-(4-aminophenyl)-6-amino-benzimidazole (0.195 g, 0.87 mmole) and t-butylacetyl chloride (0.302 ml, 0.292 g, 2.175 mmol). The resulting solid (42.3 mg) was purified by preparative HPLC.

S-2

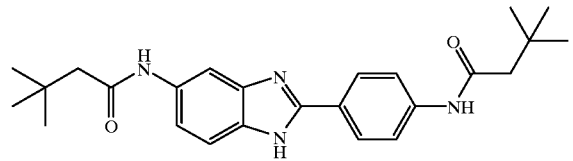

(2)

(3) Bis-cyclopentylcarbonyl benzimidazole was prepared by Method A from 2-(4-aminophenyl)-6-amino-benzimidazole (0.195 g, 0.87 mmole) and cyclopentylcarbonyl chloride (0.227 ml, 0.228 g, 2.175 mmol). The resulting solid (42.3 mg) was purified by preparative HPLC.

S-3

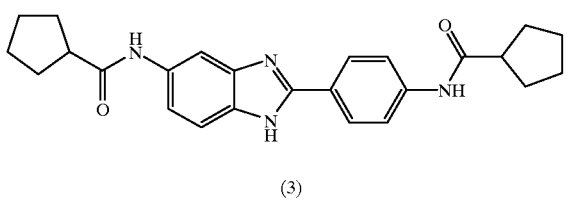

(3)

(4) Bis-adamantylcarbonyl benzimidazole was prepared by Method C from 2-(4-aminophenyl)-6-amino-benzimidazole (0.500 g, 2.23 mmole) and adamantylcarbonyl chloride (1.063 g, 5.35 mmol). The resulting solid was purified by preparative HPLC to give about 100 mg of 97% pure material.

S-28

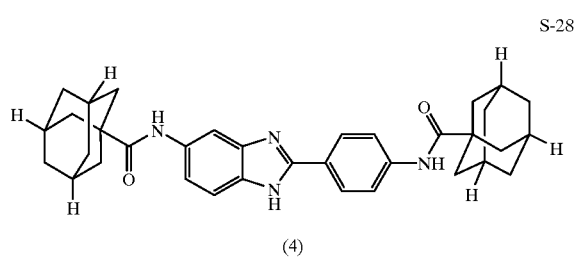

(4)

(5) Bis-cyclopropylcarbonyl benzimidazole was prepared by Method C from 2-(4-aminophenyl)-6-amino-benzimidazole (0.500 g, 2.23 mmole) and cyclopropylcarbonyl chloride (0.485 ml, 0.559 g, 5.35 mmol). The resulting solid was purified on silica gel (5% MeOH in CH$_2$Cl$_2$). HPLC shows product is 94% pure.

S-29

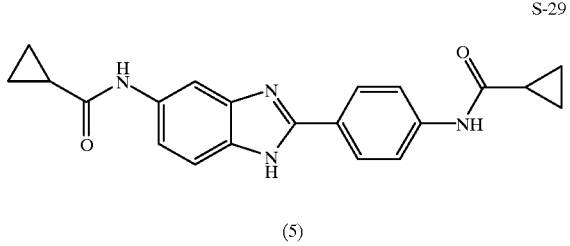

(5)

(6) Bis-cyclobutylcarbonyl benzimidazole was prepared by Method C from 2-(4-aminophenyl)-6-amino-benzimidazole (0.500 g, 2.23 mmole) and cyclobutylcarbonyl chloride (0.610 ml, 0.634 g, 5.35 mmol). The resulting solid was purified on silica gel (5% MeOH in CH$_2$Cl$_2$). HPLC shows product is 97.4% pure.

S-30

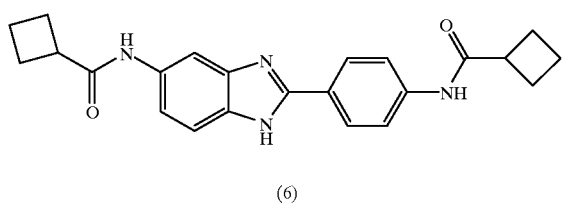

(6)

(7) Bis-trimethylacetyl Benzimidazole was prepared by method C from 2-(4-Aminophenyl)-6-amino-benzimidazole (0.500 g, 2.23 mmole) and trimethylacetyl chloride (0.610 ml, 0.634 g, 5.35 mmol). The resulting solid was purified by recrystalization (acetone/hexane) and shown to be 95% pure by HPLC.

S-137

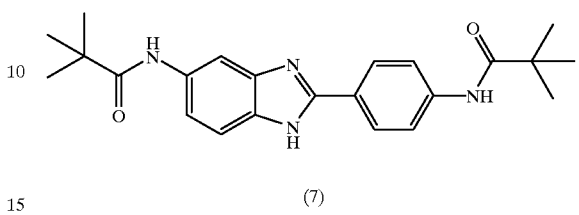

(7)

(8) Bis-2-thiopheneacetyl benzimidazole was prepared by method C from 2-(4-aminophenyl)-6-amino-benzimidazole (0.500 g, 2.23 mmole) and thiopheneacetyl chloride (0.660 ml, 0.860 g, 5.35 mmol). The resulting solid was purified on silica gel (5% MeOH in CH$_2$Cl$_2$). HPLC shows the product is 92% pure.

S-4

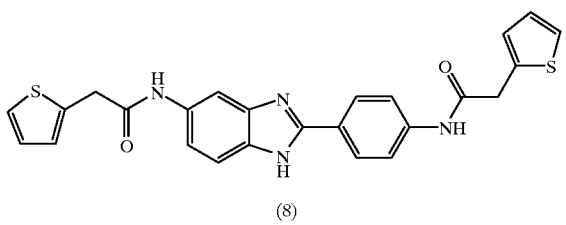

(8)

(9) Bis-cycloheptanecarbonyl benzimidazole was prepared by method C from 2-(4-aminophenyl)-6-amino-benzimidazole (0.500 g, 2.23 mmole) and cycloheptanecarbonyl chloride (0.610 ml, 0.634 g, 5.35 mmol). The resulting solid was purified by preparative HPLC to give a solid that was 98.8% pure. The cycloheptanecarbonyl chloride was synthesized as follows: cycloheptane carboxylic acid (1.37 ml, 1.42 g, 10 mmole) was added to a dried 25 ml round bottom flask and purged with N$_2$. To the flask was added oxalyl chloride (7.5 ml, 2 M in CH$_2$Cl$_2$) via syringe followed by one drop DMF. The reaction was stirred at RT overnight and the reaction concentrated under vacuum. Methylene/chloride (5 ml) was added and concentrated under vacuum to remove residual oxalyl chloride (repeated 5 times).

S-5

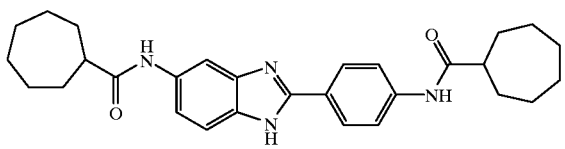

(9)

(10) Bis-(N-trifluoroacetylproline) benzimidazole was prepared by method A except that CH$_2$Cl$_2$ used as solvent from 2-(4-aminophenyl)-6-amino-benzimidazole (0.448 g, 2.0 mmole) and (s)-(–)-N-trifluoroacetylproline chloride (42.0 ml, 0.1 M in CH₂Cl₂). The resulting solid was purified on silica gel (5% MeOH in CH₂Cl₂). HPLC showed the product was 98.5% pure.

combined organic extracts were concentrated under vacuum to give a solid which was 95.6% pure by HPLC.

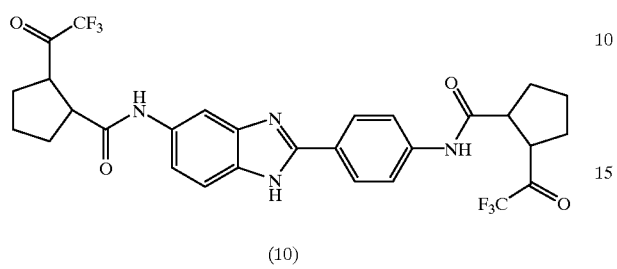

(10)

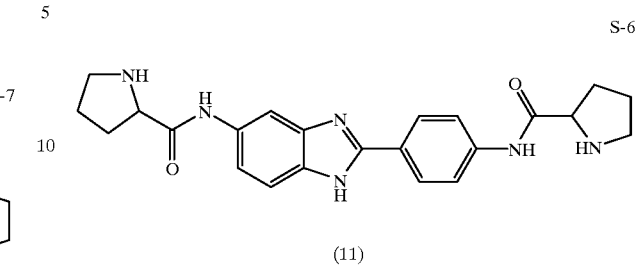

(11)

(11) Bis-proline benzimidazole was synthesized by dissolving the bis-trifluoroacetyl derivative in MeOH (5 ml) to which was added a LiOH solution (0.210 g in 5 ml water). The above mixture was heated to 42° C. for 2 hours. The reaction mixture was extracted with CH₂Cl₂ (5×15 ml). The

(12) Bis-trans-2-phenyl-cyclopropanecarbonyl benzimidazole was prepared by method C from 2-(4-aminophenyl)-6-amino-benzimidazole (0.500 g, 2.23 mmole) and trans-2-phenyl-1-cyclopropanecarbonyl chloride (0.831 ml, 0.966 g, 5.35 mmole). The resulting solid was purified on silica gel (5% MeOH in CH₂Cl₂). HPLC showed the product was 95.5% pure.

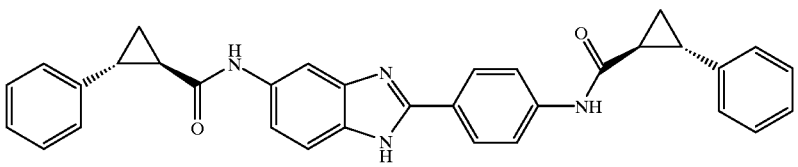

(12)

(13) Bis4-t-butylcyclohexyl carbonyl benzimidazole was prepared by method C from 2-(4-aminophenyl)-6-amino-benzimidazole (0.425 g, 1.89 mmole) and 4-t-butylcyclohexylcarbonyl chloride (0.814 g, 4.25 mmole). The resulting solid was purified on silica gel (5% MeOH in CH₂Cl₂). HPLC showed the product was 90% pure.

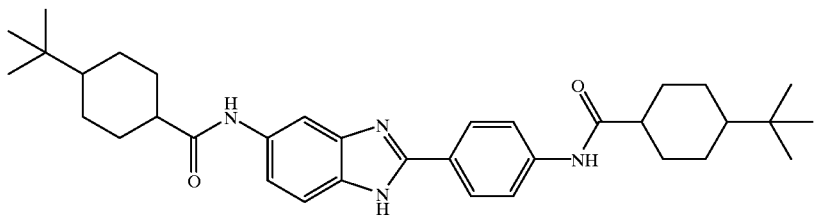

(13)

(14) Bis-1-phenylcyclohexyl carbonyl benzimidazole was prepared by method C from 2-(4-aminophenyl)-6-amino-benzimidazole (0.467 g, 2.08 mmole) and 1-phenyl-cyclohexylcarbonyl chloride (1.046 g). The resulting solid was purified on silica gel (5% MeOH in $CH_2Cl_2$). HPLC showed the product was 93.3% pure.

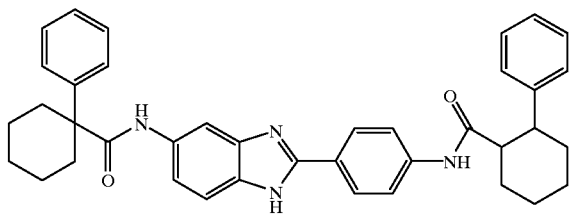

(14)

(15) Bis-trans-4-pentylcyclohexyl carbonyl benzimidazole was synthesized as follows: oxalyl chloride (1.07 ml, 2 M in $CH_2Cl_2$) was added to trans-4-pentylcyclohexyl carboxylic acid (0.424 g, 2.14 mmole) followed by one drop DMF. The mixture was allowed react at RT for 1 hour. To the above solution was added 2-(4-aminophenyl)-6-amino-benzimidazole (0.200 g, 0.89 mmole) in pyridine (2 ml). The

(16) Bis-1-phenylcyclopropane carbonyl benzimidazole was prepared by method C from 2-(4-aminophenyl)-6-amino-benzimidazole (0.530 g, 2.36 mmole) and 1-phenyl-cyclopropanecarbonyl chloride (0.9625 g, 5.3 mmole). The resulting solid was purified on silica gel (5% MeOH in $CH_2Cl_2$). HPLC showed the product was 93.4% pure.

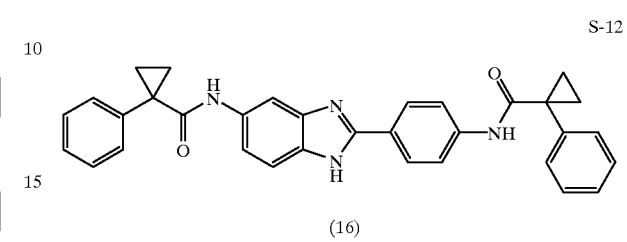

(16)

(17) Bis-(2,2,3,3-tetramethylcyclopropane)carbonyl benzimidazole was synthesized as follows: oxalyl chloride (1.07 ml, 2 M in $CH_2Cl_2$) was added to 2,2,3,3-tetramethylcyclopropane carboxylic acid (0.305 g, 2.14 mmole) followed by one drop DMF. The mixture was allowed to react at RT for 1 hour. To the above solution was added. 2-(4-aminophenyl)-6-amino-benzimidazole (0.200 g, 0.89 mmole) in pyridine (2 ml). The reaction was heated to

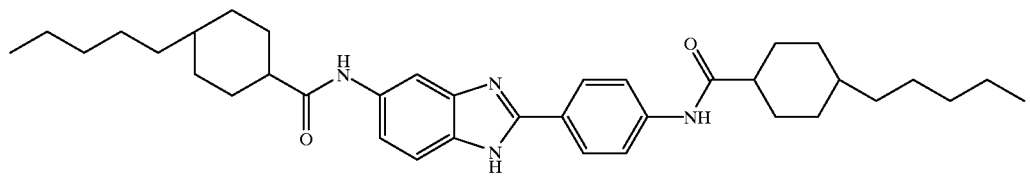

(15)

reaction was heated to 60° C. overnight. The reaction was cooled and the precipitate filtered and washed with $NaHCO_3$ and hexanes. The resulting solid was purified by preparative HPLC to yield a solid which was >99% pure.

60° C. overnight. The reaction was cooled and the precipitate filtered and washed with $NaHCO_3$ and hexanes. The resulting solid was purified by preparative HPLC to yield a solid that was >99% pure.

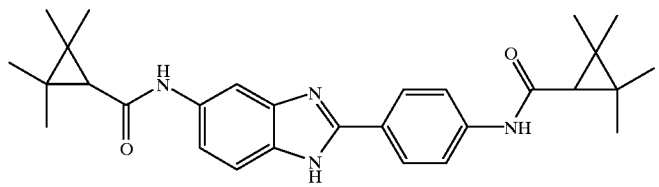

(17)

(18) Bis-4-methylcyclohexyl carbonyl benzimidazole was prepared by method D from 2-(4-aminophenyl)-6-amino-benzimidazole (0.100 g, 0.44 mmole) and 4-methylcyclohexylcarboxylic acid (0.138 g, 0.96 mmole). The resulting solid was purified on silica gel (5% MeOH in CH$_2$Cl$_2$). HPLC showed the product was 94.5% pure.

S-54

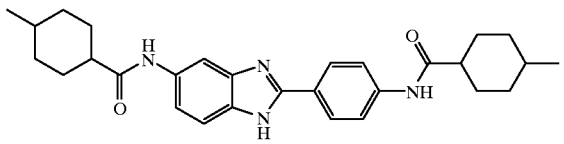

(18)

(19) Bis-1-phenylcyclohexyl carbonyl benzimidazole was synthesized as follows: oxalyl chloride (1.07 ml, 2 M in CH$_2$Cl$_2$) was added to 1-methylcyclo hexanecarboxylic acid (0.305 g, 2.14 mmole) followed by one drop DMF. The mixture was allowed to react at RT for 1 hour. To the above solution was added 2-(4-aminophenyl)-6-amino-benzimidazole (0.200 g, 0.89 mmole) in pyridine (2 ml). The reaction was heated to 60° C. overnight.

S-58

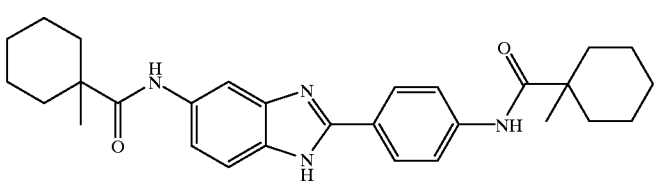

(19)

The reaction was cooled and the precipitate filtered and washed with NaHCO$_3$ and hexanes. The resulting solid was purified by preparative HPLC to give a solid that was >99% pure.

(20) Bis-bicyclo[2.2.1]heptane-2-carbonyl benzimidazole was prepared as follows: oxalyl chloride (1.07 ml, 2 M in CH$_2$Cl$_2$) was added to bicyclo[2.2.1]heptanecarboxylic acid (0.305 g, 2.14 mmole) followed by one drop DMF. The mixture was allowed to react at RT for 1 hour. To the above solution was added 2-(4-aminophenyl)-6-amino-benzimidazole (0.200 g, 0.89 mmole) in pyridine (2 ml). The reaction was heated to 60° C. overnight. The reaction was cooled and the precipitate filtered and washed with NaHCO$_3$ and hexanes. The resulting solid was purified by preparative HPLC to give a solid that was 68% pure.

S-17

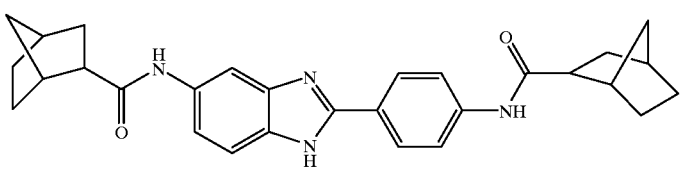

(20)

(21) Bis-4-methoxycyclohexyl carbonyl benzimidazole was synthesized as follows: oxalyl chloride (1.07 ml, 2 M in CH₂Cl₂) was added to 4-methoxy-1-cyclohexane carboxylic acid (0.338 g, 2.14 mmole) followed by one drop DMF. The mixture was allowed to react at RT for 1.0 hour. To the above solution was added 2-(4-aminophenyl)-6-amino-benzimidazole (0.200 g, 0.89 mmole) in pyridine (2 ml). The reaction was heated to 60° C. overnight. The reaction was cooled and the precipitate filtered and washed with NaHCO₃ and hexanes.

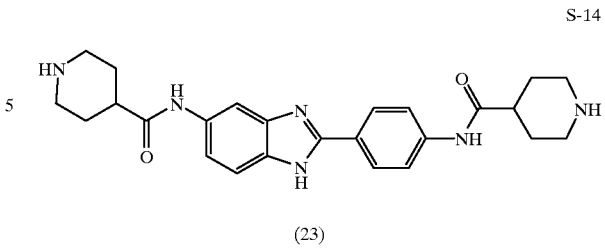

(23)

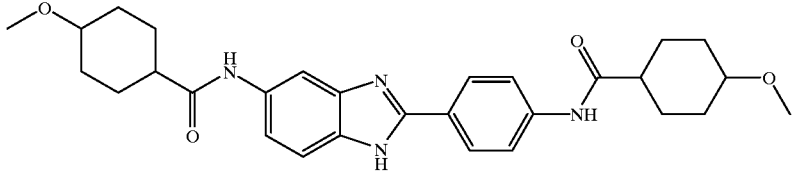

(21)

(22) Bis-3-thiopheneacetyl benzimidazole was produced as follows: oxalyl chloride (1.07 ml, 2 M in CH₂Cl₂) was added to 3-thiopheneacetic acid (0.338 g, 2.14 mmole) followed by one drop DMF. The mixture was allowed to react at RT for 1.0 hour. To the above solution was added 2-(4-aminophenyl)-6-amino-benzimidazole (0.200 g, 0.89 mmole) in pyridine (2 ml). The reaction was heated to 60° C. overnight. The reaction was cooled and the precipitate filtered and washed with NaHCO₃ and hexanes.

Monoacyl Benzimidazole Inhibitors of IgE

A family of IgE inhibitors related to the diacyl compounds described above are asymmetrical monoacylated benzimidazole compounds. Several monoacyl variations were synthesized; these are disclosed below:

(1) 2-(N-Cyclohexanecarbonyl-4-aminophenyl)-5-trifluoromethyl benzimidazole was synthesized from the following series of benzimidazole intermediates:. 1) 2-(4-nitrophenyl)-5-trifluoromethyl benzimidazole (designated 1.1) and 2) 2-(4-aminophenyl)-5-trifluoromethyl benzimidazole (designated 1.2).

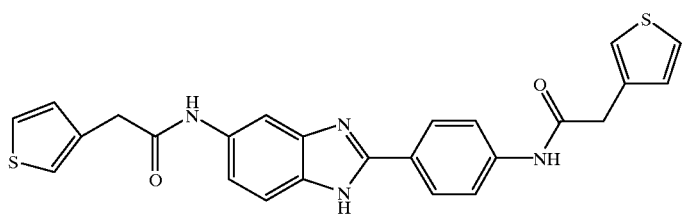

(22)

(23) Bis-4-nipecotamide benzimidazole was produced as follows: Bis-N-Boc-4-nipecotamide benzimidazole (0.400 g) was dissolved in 1:1 TFA:CH₂Cl₂ (4 ml) at −20° C. overnight. The solvent was removed under vacuum and water added, frozen on dry ice and lyophilized to dryness. The Boc-protected benzimidazole was synthesized as follows: oxalyl chloride (2.82 ml, 2 M in CH₂Cl₂) was added to N-Boc-nipecotic acid (1.293 g, 5.64 mmole) followed by one drop DMT. The mixture was allowed to react at RT for 1.0 hour. To the above solution was added. 2-(4-aminophenyl)-6-amino-benzimidazole (0.500 g, 2.24 mmole) in pyridine (5 ml). The reaction was heated to 60° C. overnight. The reaction was cooled and the precipitate filtered and washed with NaHCO₃ and hexanes. The resulting solid was found to be >99% pure by HPLC.

(1.1) 2-(4-Nitrophenyl)-5-trifluoromethyl benzimidazole was synthesized as follows: 1,2-diamino-4-trifluoromethylbenzene (1.76 g, 10.0 mmole) was mixed with 4-nitrobenzoic acid (1.67 g, 9.8 mmole), dissolved in POCl₃ (12 ml), and heated to reflux for 2.5 hours. The reaction mixture was cooled and cautiously poured onto ice. The resulting solid was filtered, washed with NaHCO₃ and used without further purification.

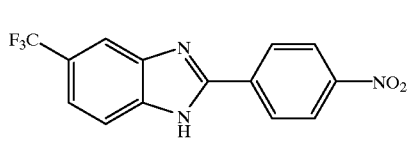

(1.1)

(1.2) 2-(4-Aminophenyl)-5-trifluoromethyl benzimidazole was produced from 2-(4-nitrophenyl)-5-trifluoromethyl benzimidazole (1.1; see above). The crude 2-(4-nitrophenyl)-5-trifluoromethyl benzimidazole filtrate was dissolved in conc. HCl (15 ml) to which was added $SnCl_2.H_2O$ (13.5 g, 59 mmol) and heated to reflux for 16 h. The reaction was cooled and the HCl salt precipitated by the addition of EtOH (75 ml).

The solid was filtered, washed with ethanol, and dissolved in water. The salt was neutralized by the addition of conc. ammonium hydroxide and the free base isolated by filtration. The product was characterized by mass spectroscopy.

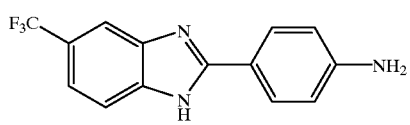

(1.2)

(1) 2-(N-Cyclohexanecarbonyl-4-aminophenyl)-5-trifluoromethyl benzimidazole was prepared from the amino, 2-(4-aminophenyl)-5-trifluoromethyl benzimidazole (1.2; see above). The amine (0.239 g, 0.86 mmol) was dissolved in $THF:H_2O$ (5 ml, 1:1) followed by $K_2CO_3$ (0.1213 g, 0.88 mmol) and cyclohexyl carbonyl chloride (130 μL, 0.95 mmol). The reaction mixture was shaken for 23 h at room temperature. Sodium chloride was added to the reaction and the mixture extracted with EtOAc. The combined organic extracts were washed with water, dried over $Na_2SO_4$ and concentrated under vacuum. The resulting solid was purified by preparative TLC (10% MeOH in $CH_2Cl_2$).

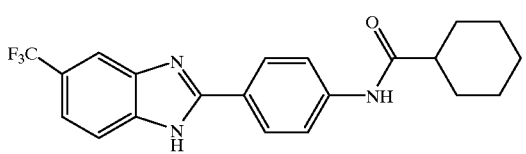

S-138

(1)

The next species (2), 2-(N-cyclohexanecarbonyl-4-aminophenyl)-5-fluoro benzimidazole was synthesized from the following series of benzimidazole intermediates: 1) 2-(4-nitrophenyl)-5-fluoro benzimidazole (designated 2.1) and 2) 2-(4-aminophenyl)-5-fluoro benzimidazole (designated 2.2).

(2.1) 2-(4-Nitrophenyl)-5-fluoro benzimidazole was synthesized as follows: 1,2-diamino-4-fluorobenzene (1.26 g, 10.0 mmole was mixed with 4-nitrobenzoic acid (1.67 g, 9.8 mmole) and dissolved in $POCl_3$ (10 ml) and heated to reflux for 2.5 hours. The reaction mixture was cooled and cautiously poured onto ice. The resulting solid was filtered, washed with $NaHCO_3$ and used without further purification.

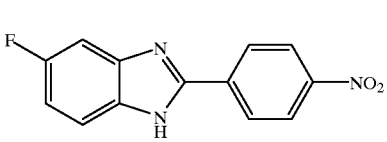

(2.1)

(2.2) 2-(4-Aminophenyl)-5-fluoro benzimidazole was prepared by dissolving 1 g of the above nitrobenzimidazole (2.1) in 30% $Na_2S.9H_2O$ (20 ml) with stirring at RT for 24 h. The reaction mixture was diluted with water and extracted with EtOAc. The combined organic extracts were dried over sodium sulfate and concentrated under vacuum. The product was characterized by mass spectroscopy.

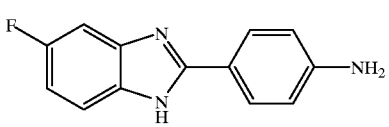

(2.2)

(2) 2-(N-Cyclohexanecarbonyl-4-aminophenyl)-5-fluoro benzimidazole was prepared by dissolving 0.100 g (0.44 mmol) of the above amine (2.2) in pyridine (1 ml) followed by cyclohexanecarbonyl chloride (63.2 μl) and heated to 60° C. overnight. The reaction was diluted with water (8 ml) and extracted with EtOAc. The combined organic fractions were combined, dried ($Na_2SO_4$) and concentrated under vacuum. The resulting solid was purified by flash chromatography (5% $MeOH/CH_2Cl_2$).

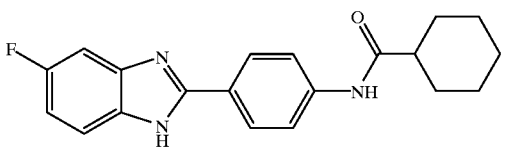

S-139

(2)

The next species (3), 2-(N-3',4'-dichlorobenzoyl-4-aminophenyl)-3,4-dimethyl benzimidazole was synthesized from the following series of benzimidazole intermediates: 1) 2-(4-nitrophenyl)-4,5-dimethyl benzimidazole (designated 3.1) and 2) 2-(4-aminophenyl)-4,5-dimethyl benzimidazole (designated 3.2).

(3.1) 2-(4-Nitrophenyl)-4,5-dimethyl benzimidazole was prepared by mixing 1,2-diamino-3,4-dimethylbenzene (1.36 g, 9.8 mmole with 4-nitrobenzoic acid (1.67 g, 9.8 mmole) and dissolved in $POCl_3$ (10 ml) and heated to reflux for 2.5 hours. The reaction mixture was cooled and cautiously poured onto ice. The resulting solid was filtered, washed with $NaHCO_3$ and used without further purification.

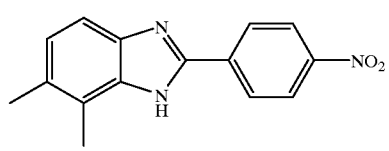

(3.1)

(3.2) 2-(4-Aminophenyl)-4,5-dimethyl benzimidazole was synthesized by dissolving 1.0 g of the above nitrobenzimidazole (3.1) in 30% Na$_2$S.9H$_2$O (20 ml) and stirring at RT for 2.5 h. The reaction mixture was diluted with water and extracted with EtOAc. The combined organic extracts were dried over sodium sulfate and concentrated under vacuum. The product was characterized by mass spectroscopy.

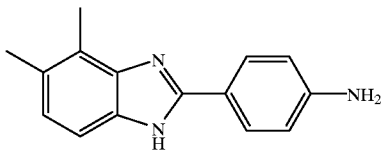

(3.2)

(3) 2-(N-Cyclohexanecarbonyl-4-aminophenyl)-3,4-dimethyl benzimidazole was prepared by dissolving 0.0954 g (0.402 mmol) of the above amine (3.2) in 1.0 ml of pyridine followed by cyclohexanecarbonyl chloride (57.6 μl) and heated to 60° C. overnight. The reaction was diluted with water (8 ml) and extracted with EtOAc. The combined organic fractions were combined, dried Na$_2$SO$_4$) and concentrated under vacuum. The resulting solid was purified by flash chromatography (5% MeOH/CH$_2$Cl$_2$).

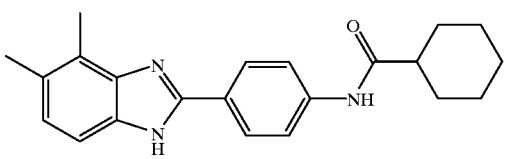

S-140

(3)

Suppression of IgE Response

The inhibitory activity of the small molecules of the present invention were assayed using both the ex vivo and in vivo assays as described above. All of the compounds presented above were active in suppressing the IgE response. In the ex vivo assay, compounds produced 50% inhibition at concentrations ranging from 1 pM to 10 μM. In the in vivo assay, the compounds were effective at concentrations ranging from less than about 0.01 mg/kg/day to about 25 mg/kg/day, when administered in divided doses (e.g., two to four times daily) for at least two to seven consecutive days. The diacyl benzimidazole compounds were generally more potent than the monoacyl compounds. Thus, the small molecule inhibitors of the present invention are disclosed as being useful in lowering the antigen-induced increase in IgE concentration, and consequently, in the treatment of IgE-dependent processes such as allergies in general and allergic asthma in particular.

Treatment Regimens

The amount of the IgE inhibitor compound which may be effective in treating a particular allergy or condition will depend on the nature of the disorder, and can be determined by standard clinical techniques. The precise dose to be employed in a given situation will also depend on the choice of compound and the seriousness of the condition, and should be decided according to the judgment of the practitioner and each patient's circumstances. Appropriate dosages can be determined and adjusted by the practitioner based on dose response relationships between the patient's IgE levels as well as standard indices of pulmonary and hemodynamic changes. Moreover, those skilled in the art will appreciate that dose ranges can be determined without undue experimentation by following the protocol(s) disclosed herein for ex vivo and in vivo screening (See for example Hasegawa et al., *J. Med. Chem.* 40: 395–407 (1997) and Ohmori et al., *Int. J. Immunopharmacol.* 15:573–579 (1993); employing similar ex vivo and in vivo assays for determining dose-response relationships for IgE suppression by naphthalene derivatives; incorporated herein by reference).

Initially, suitable dosages of the compounds will generally range from about 0.001 mg to about 300 mg per kg body weight per day in divided doses, more preferably, between about 0.01 mg and 100 mg per kg body weight per day in divided doses. The compounds are preferably administered systemically as pharmaceutical formulations appropriate to such routes as oral, aerosol, intravenous, subcutaneously, or by any other route which may be effective in providing systemic dosing of the active compound. The compositions of pharmaceutical formulations are well known in the art. The treatment regimen preferably involves periodic administration. Moreover, long-term therapy may be indicated where allergic reactions appear to be triggered by continuous exposure to the allergen(s). Daily or twice daily administration has been effective in suppressing the IgE response to a single antigen challenge in animals when carried out continuously from a period of two to seven consecutive days. Thus, in a preferred embodiment, the compound is administered for at least two consecutive days at regular periodic intervals. However, the treatment regimen, including frequency of dosing and duration of treatment may be determined by the skilled practitioner, and modified as needed to provide optimal IgE down-regulation, depending on nature of the allergen, the dose, frequency, and duration of the allergen exposure, and the standard clinical indices.

In one embodiment of the present invention, an IgE-suppressing compound may be administered in conjunction with one or more of the other small molecule inhibitors disclosed, in order to produce optimal down-regulation of the patient's IgE response. Further, it is envisioned that one or more of the compounds of the present invention may be administered in combination with other drugs already known or later discovered for treatment of the underlying cause as well as the acute symptoms of allergy or asthma. Such combination therapies envisioned within the scope of the present invention include mixing of one or more of the small molecule IgE-inhibitors together with one or more additional ingredients, known to be effective in reducing at least one symptom of the disease condition. In a variation, the small molecule IgE-inhibitors herein disclosed may be administered separately from the additional drugs, but during the same course of the disease condition, wherein both the IgE-inhibitor(s) and the palliative compounds are administered in accordance with their independent effective treatment regimens.

While a number of preferred embodiments of the invention and variations thereof have been described in detail, other modifications and methods of use will be readily apparent to those of skill in the art. Accordingly, it should be understood that various applications, modifications and substitutions may be made of equivalents without departing from the spirit of the invention or the scope of the claims.

What is claimed is:

1. A pharmaceutical composition for treating or preventing an allergic reaction associated with increased IgE levels in a mammal comprising one or more of the following compounds:

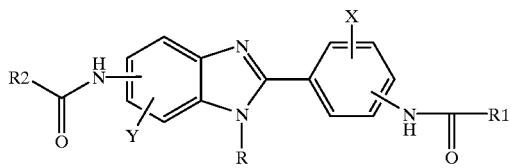

(A)

wherein X and Y are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and NHCOR1;

wherein R is selected from the group consisting of H, $CH_3$, $C_2H_5$, $C_3H_7$, $C_4H_9$, $CH_2Ph$, and $CH_2C_6H4$—F (p-);

wherein R1 and R2 are independently selected from the group consisting of alkyl, cycloalkyl, substituted cycloalkyl, multi-ring cycloalkyl, fused-ring aliphatic, cyclopropyl, substituted cyclopropyl, cyclobutyl, substituted cyclobutyl, cyclopentyl, substituted cyclopentyl, cyclohexyl, substituted cyclohexyl, cycloheptyl, substituted cycloheptyl, bicycloheptyl, bicyclooctyl, bicyclononyl, substituted bicycloalkenyl, adamantyl, and substituted adamantyl, wherein said substitutions are not heterocyclic rings; and wherein the substitutes on said substituted cycloalkyl, substituted cyclopropyl, substituted cyclobutyl, substituted cyclopentyl, substituted cyclohexyl, substituted cycloheptyl, substituted bicycloalkenyl, and substituted adamantyl are selected from the group consisting of alkyl, aryl, $CF_3$, $CH_3$, $OCH_3$, OH, CN, $COOR_5$ and COOH.

2. The pharmaceutical composition of claim 1, further comprising at least one additional ingredient which is active in reducing at least one symptom associated with said allergic reaction.

3. The pharmaceutical composition of claim 2, wherein said at least one additional ingredient is selected from the group consisting of a short-acting $\beta_2$-adrenergic agonist, a long-acting $\beta_2$-adrenergic agonist, an antihistamine, a phosphodiesterase inhibitor, an anticholinergic agent, a corticosteroid, an inflammatory mediator release inhibitor and a leukotriene receptor antagonist.

4. A method for treating or preventing an allergic reaction in a mammal wherein said reaction is caused by an increase in IgE levels comprising administering an IgE-suppressing amount of at least one compound of claim 1.

5. The method of claim 4 further comprising administering at least one additional ingredient which is active in reducing at least one symptom associated with said allergic reaction.

6. The method of claim 5, wherein said additional ingredient is selected from the group consisting of a short-acting $\beta_2$-adrenergic agonist, a long-acting $\beta_2$-adrenergic agonist, an antihistamine, a phosphodiesterase inhibitor, an anticholinergic agent, a corticosteroid, an inflammatory mediator release inhibitor and a leukotriene receptor antagonist.

7. A method for treating or preventing asthma in a mammal comprising administering an IgE-suppressing amount of at least one compound of claim 1.

8. The method of claim 7 further comprising administering at least one additional ingredient which is active in reducing at least one symptom associated with said allergic reaction.

9. The method of claim 8, wherein said additional ingredient is selected from the group consisting of a short-acting $\beta_2$-adrenergic agonist, a long-acting $\beta_2$-adrenergic agonist, an antihistamine, a phosphodiesterase inhibitor, an anticholinergic agent, a corticosteroid, an inflammatory mediator release inhibitor and a leukotriene receptor antagonist.

10. A pharmaceutical composition for treating or preventing an allergic reaction associated with increased IgE levels in a mammal comprising one or more of the following compounds:

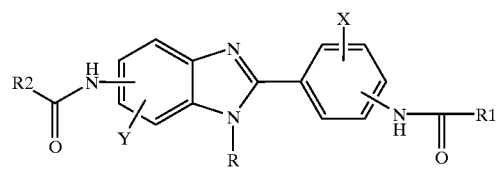

(A)

wherein X and Y are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and NHCOR1;

wherein R is selected from the group consisting of H, $CH_3$, $C_2H_5$, $C_3H_7$, $C_4H_9$, $CH_2Ph$, and $CH_2C_6H4$—F (p-);

wherein R1 and R2 are independently selected from the group consisting of alkyl, cycloalkyl, substituted cycloalkyl, multi-ring cycloalkyl, fused-ring aliphatic, cyclopropyl, substituted cyclopropyl, cyclobutyl, substituted cyclobutyl, cyclopentyl, substituted cyclopentyl, cyclohexyl, substituted cyclohexyl, cycloheptyl, substituted cycloheptyl, bicycloheptyl, bicyclooctyl, bicyclononyl, substituted bicycloalkenyl, adamantyl, and substituted adamantyl, wherein said substitutions are not heterocyclic rings; and wherein said one or more of the following compounds is selected from the group consisting of:

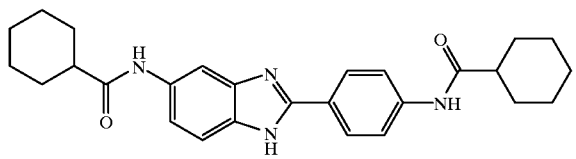

S-1

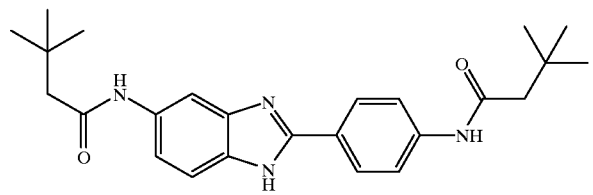

S-2

-continued
S-3
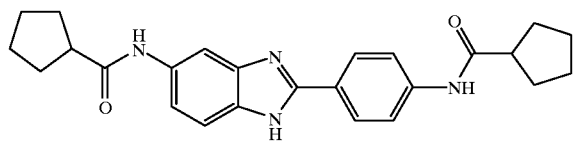
S-5
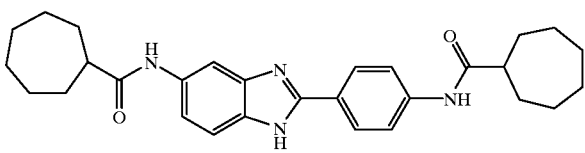
S-8
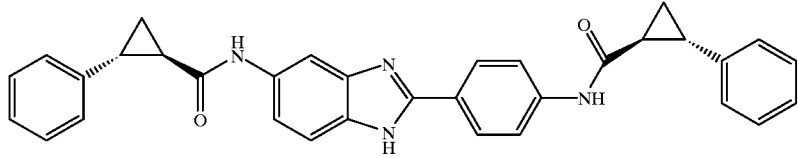
S-9
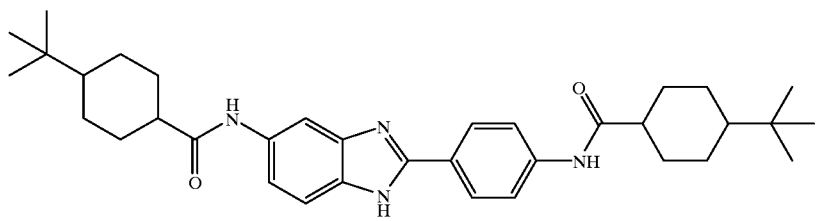
S-10
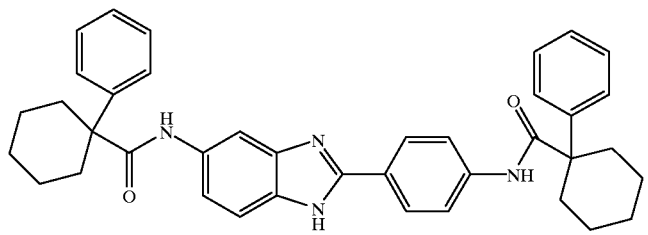
S-11
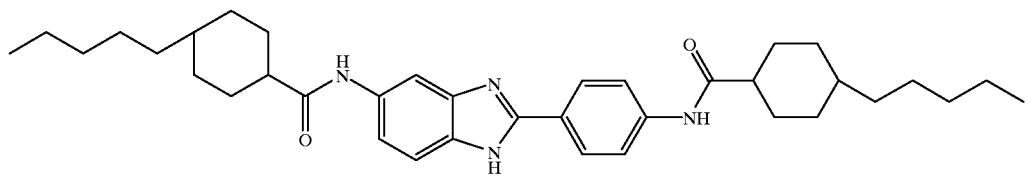
S-12
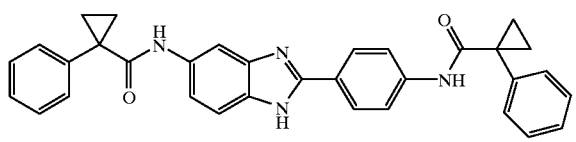
S-15
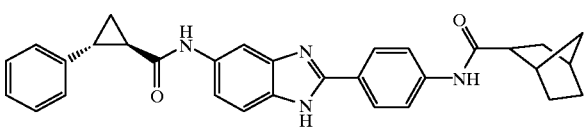
S-16
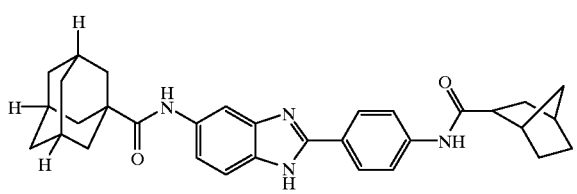
S-17
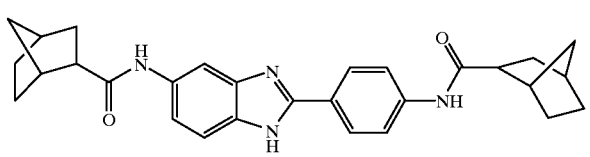

-continued

-continued
S-35
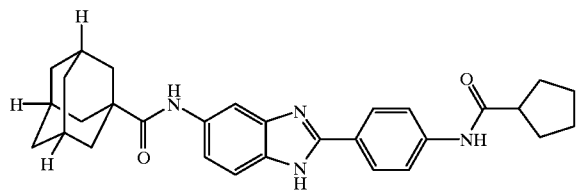
S-36
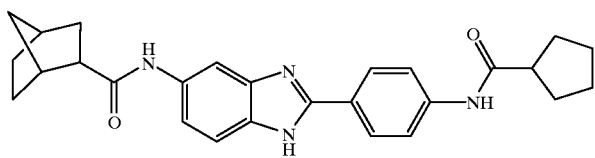
S-37
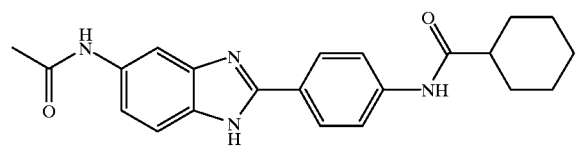
S-38
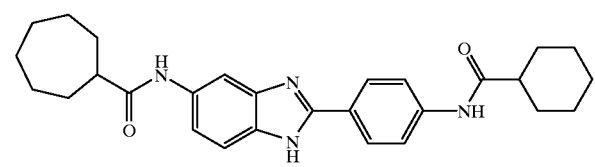
S-39
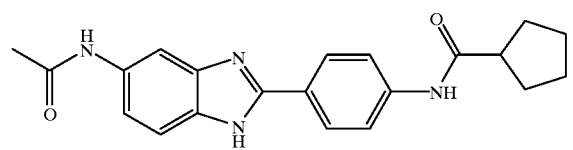
S-40
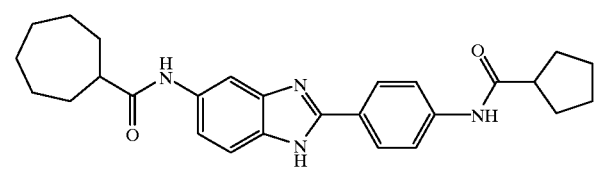
S-41
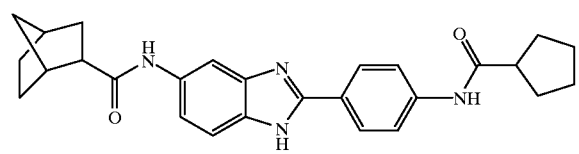
S-42
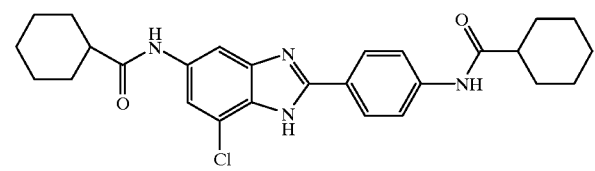
S-43
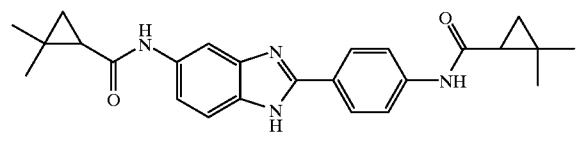
S-45
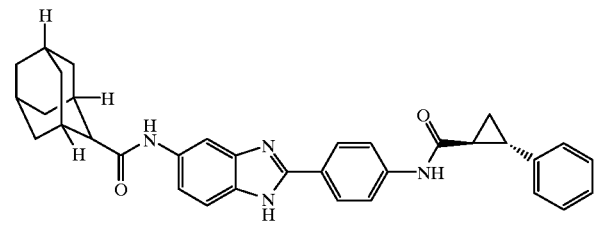
S-46
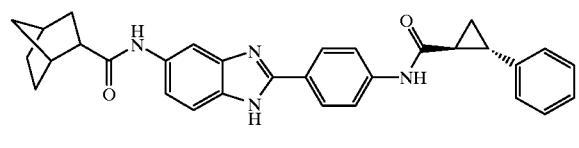
S-47
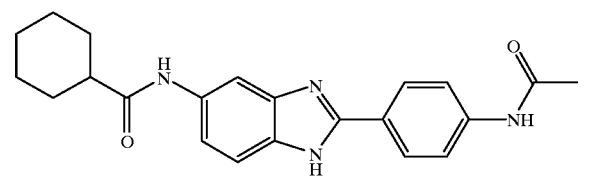
S-48
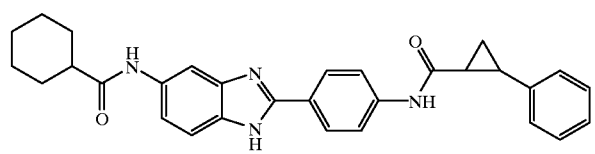
S-49
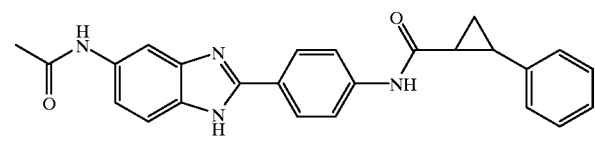

-continued
S-50
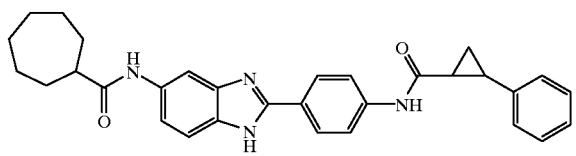
S-51
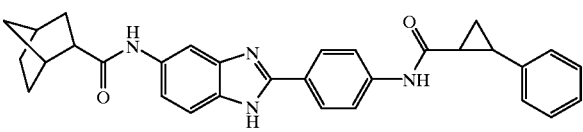
S-52
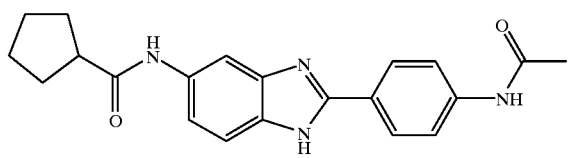
S-53
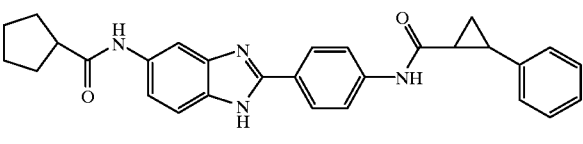
S-54
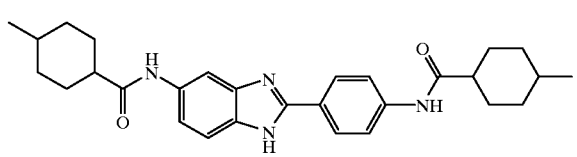
S-55
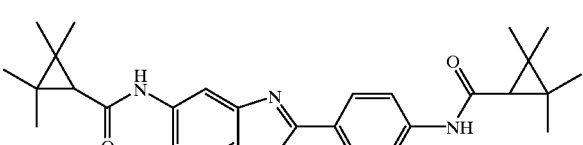
S-56
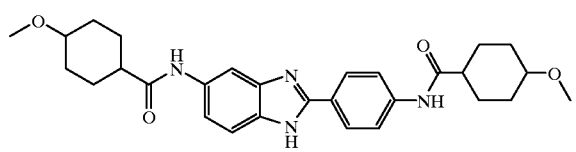
S-57
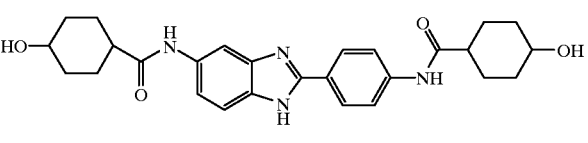
S-58
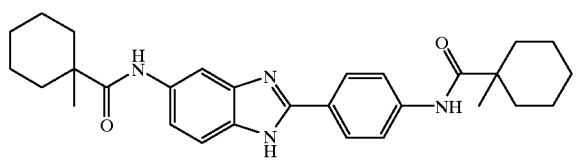
S-65
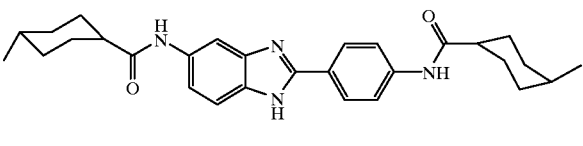
S-66
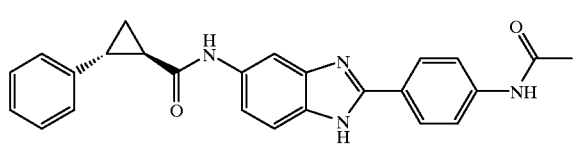
S-67
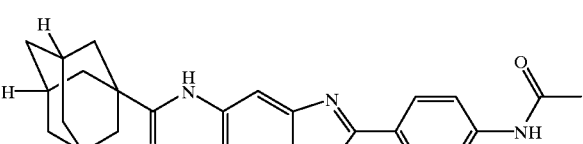
S-68
S-69
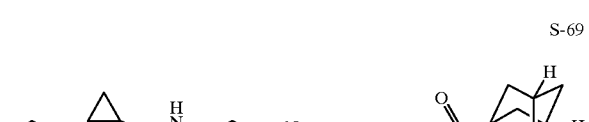
S-70
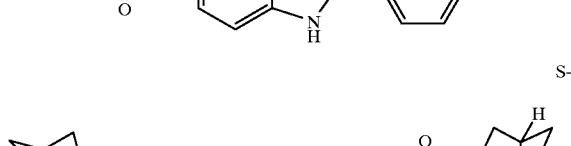
S-72
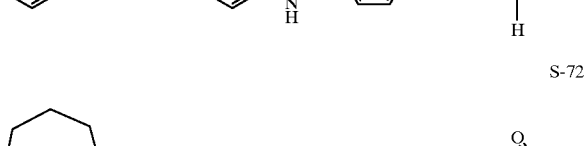

-continued
S-73
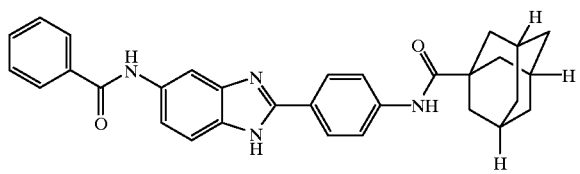
S-74
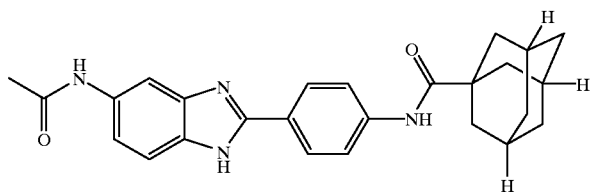
S-75
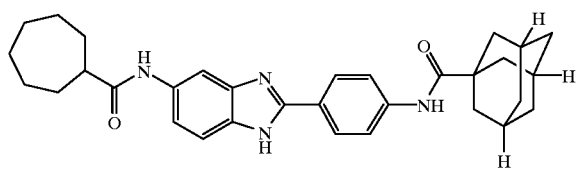
S-76
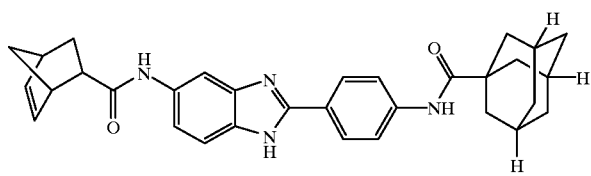
S-77
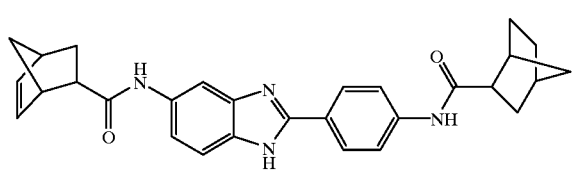
S-79
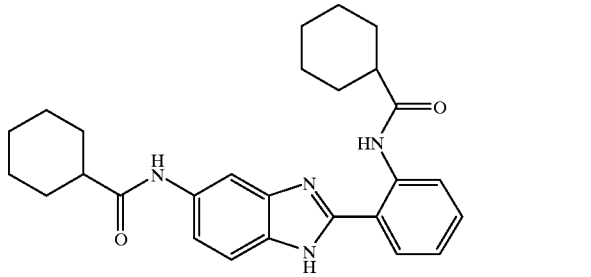
S-80
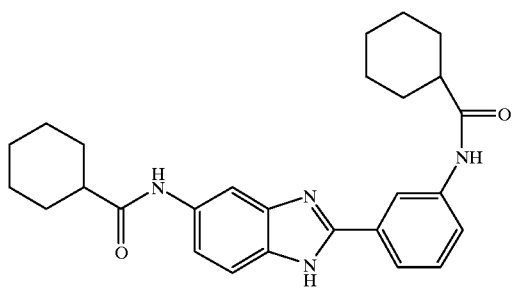
S-81
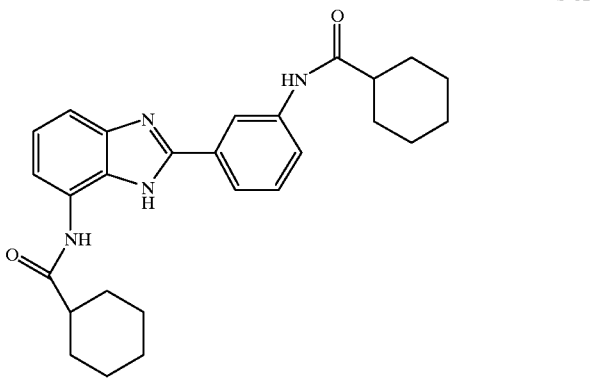
S-82
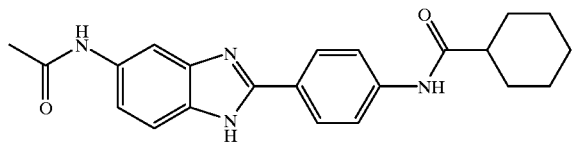
S-83
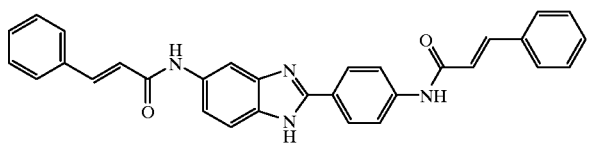
S-84
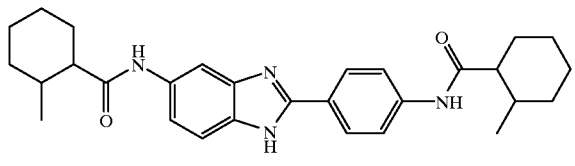
S-85
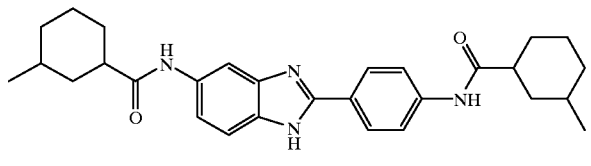

-continued
S-86
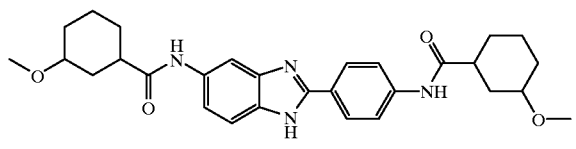
S-87
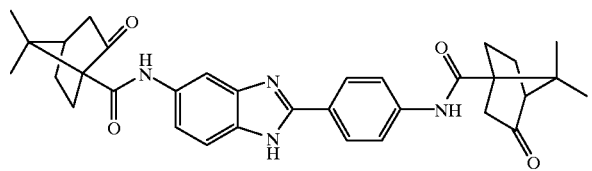
S-88
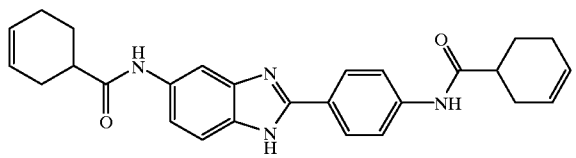
S-89
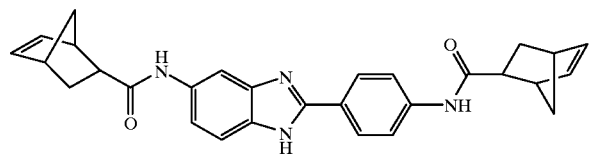
S-90
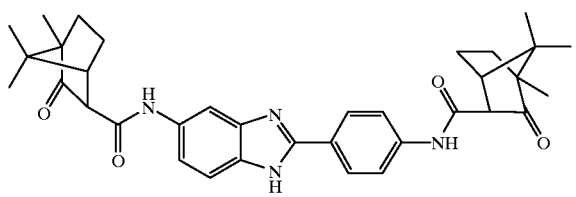
S-93
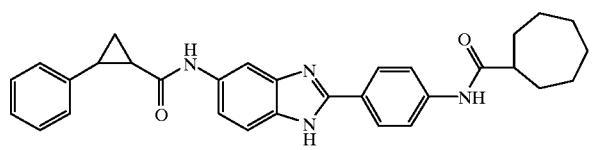
S-94
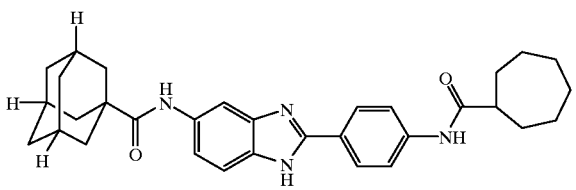
S-95
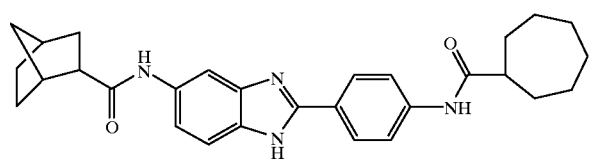
S-96
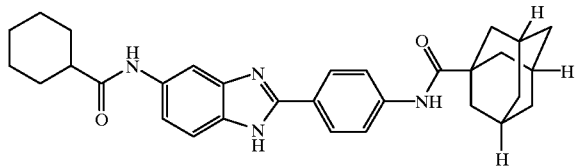
S-97
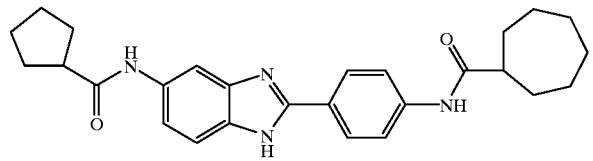
S-98
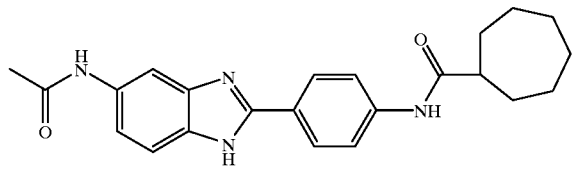
S-99
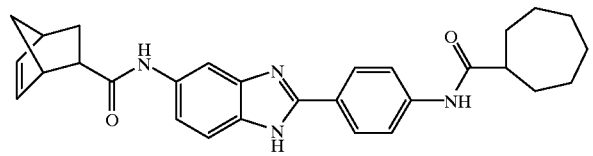
S-100
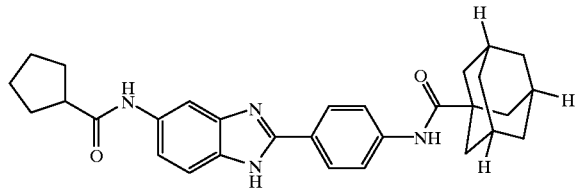
S-101
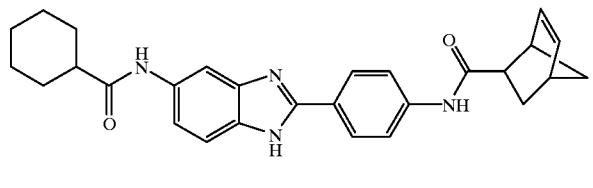

-continued

S-102 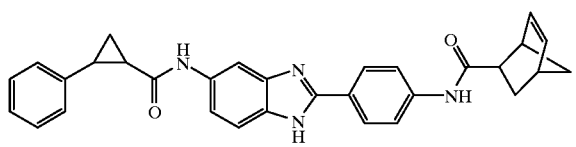 S-103 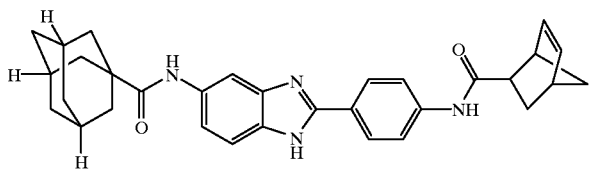

S-104 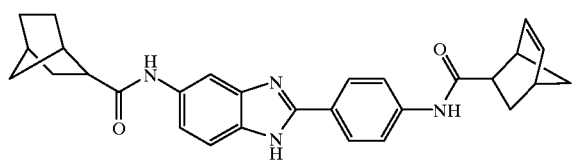 S-105 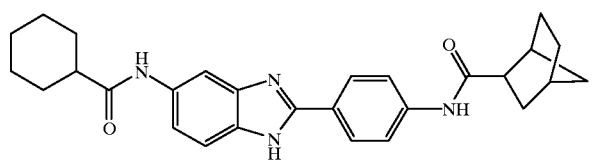

S-106 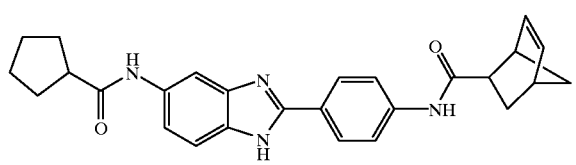 S-107 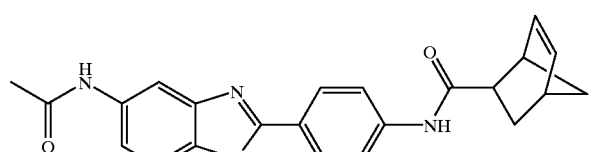

S-108 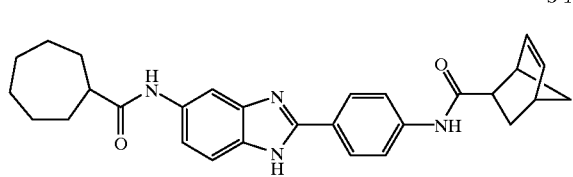 S-109 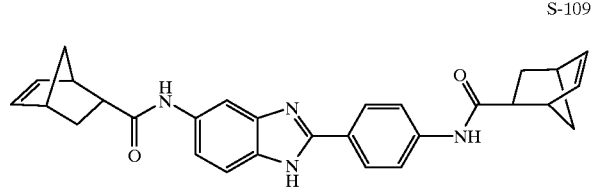

S-110

11. The pharmaceutical composition of claim 10, further comprising at least one additional ingredient which is active in reducing at least one symptom associated with said allergic reaction.

12. The pharmaceutical composition of claim 11, wherein said at least one additional ingredient is selected from the group consisting of a short-acting β2-adrenergic agonist, a long acting β2-adrenergic agonist, an antihistamine, a phosphodiesterase inhibitor, an anticholinergic agent, a corticosteroid, an inflammatory mediator release inhibitor and a leukotriene receptor antagonist.

13. A method for treating or preventing an allergic reaction in a mammal wherein said reaction is caused by an increase in IgE levels comprising administering an IgE-suppressing amount of at least one compound of claim 10.

14. The method of claim 13 further comprising administering at least one additional ingredient which is active in reducing at least one symptom associated with said allergic reaction.

15. The method of claim 14, wherein said additional ingredient is selected from the group consisting of a short-acting $\beta_2$-adrenergic agonist, a long-acting $\beta_2$-adrenergic agonist, an antihistamine, a phosphodiesterase inhibitor, an anticholinergic agent, a corticosteroid, an inflammatory mediator release inhibitor and a leukotriene receptor antagonist.

16. A method for treating or preventing asthma in a mammal comprising administering an IgE-suppressing amount of at least one compound of claim 10.

17. The method of claim 16 further comprising administering at least one additional ingredient which is active in reducing at least one symptom associated with said allergic reaction.

18. The method of claim 17, wherein said additional ingredient is selected from the group consisting of a short-acting $\beta_2$-adrenergic agonist, a long-acting $\beta_2$-adrenergic agonist, an antihistamine, a phosphodiesterase inhibitor, an anticholinergic agent, a corticosteroid, an inflammatory mediator release inhibitor and a leukotriene receptor antagonist.

* * * * *

UNITED STATES PATENT AND TRADEMARK OFFICE
CERTIFICATE OF CORRECTION

PATENT NO.   : 6,369,091 B1
DATED         : April 9, 2002
INVENTOR(S)  : Sicar et al.

It is certified that error appears in the above-identified patent and that said Letters Patent is hereby corrected as shown below:

Column 13,
Line 2, the formula should be deleted.

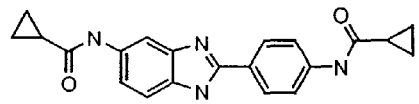

Column 14,
Line 2, the formula should be deleted.

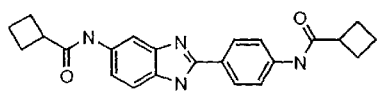

Column 19,
Line 5, the formula should be deleted.

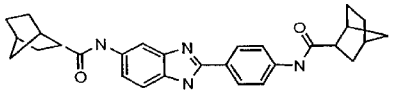

Column 21,
The following formulas should be deleted:

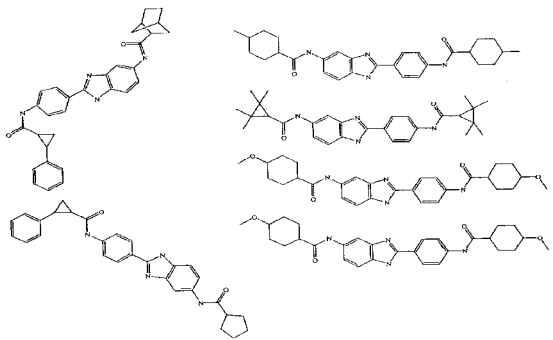

Column 22,
The following formula should be deleted:

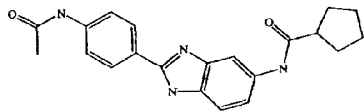

UNITED STATES PATENT AND TRADEMARK OFFICE
CERTIFICATE OF CORRECTION

PATENT NO. : 6,369,091 B1
DATED : April 9, 2002
INVENTOR(S) : Sicar et al.

It is certified that error appears in the above-identified patent and that said Letters Patent is hereby corrected as shown below:

Column 23,
The following formulas should be deleted:

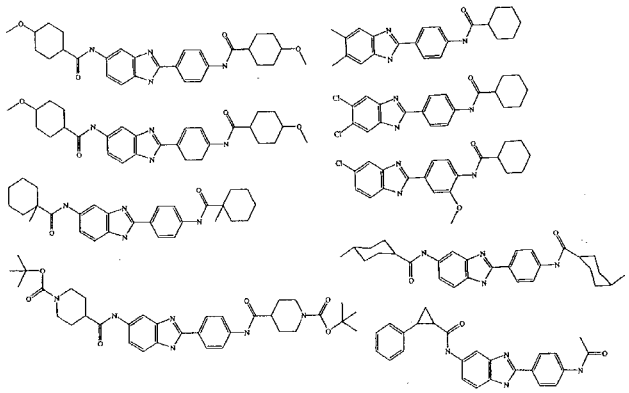

Column 24,
The following formulas should be deleted:

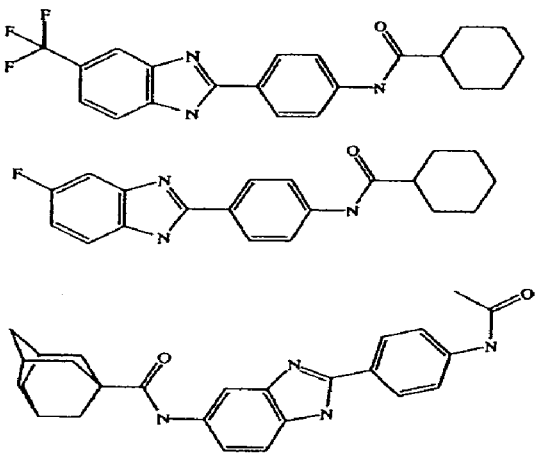

UNITED STATES PATENT AND TRADEMARK OFFICE
CERTIFICATE OF CORRECTION

PATENT NO.    : 6,369,091 B1                                                Page 3 of 10
DATED         : April 9, 2002
INVENTOR(S)   : Sicar et al.

It is certified that error appears in the above-identified patent and that said Letters Patent is hereby corrected as shown below:

Column 25,
The following formulas should be deleted:

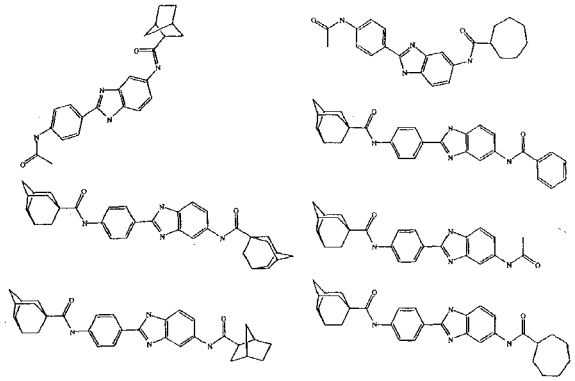

Column 26,
The following formulas should be deleted:

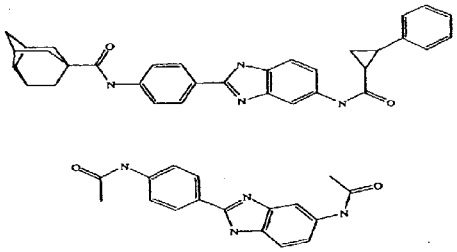

Column 27,
The following formulas should be deleted:

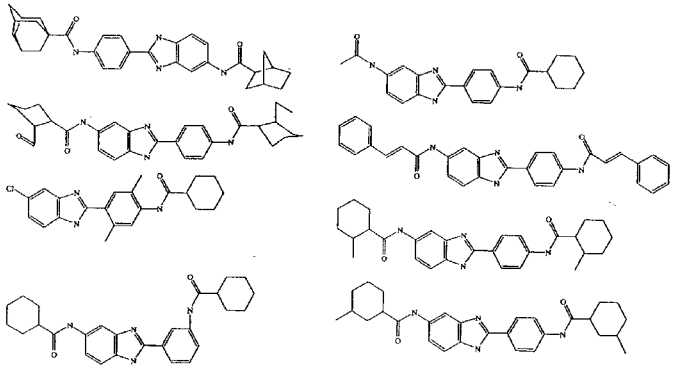

UNITED STATES PATENT AND TRADEMARK OFFICE
CERTIFICATE OF CORRECTION

PATENT NO.    : 6,369,091 B1
DATED         : April 9, 2002
INVENTOR(S)   : Sicar et al.

It is certified that error appears in the above-identified patent and that said Letters Patent is hereby corrected as shown below:

Column 28,
The following formulas should be deleted:

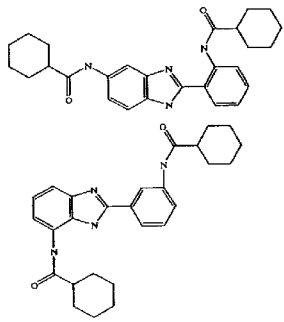

Column 29,
The following formulas should be deleted:

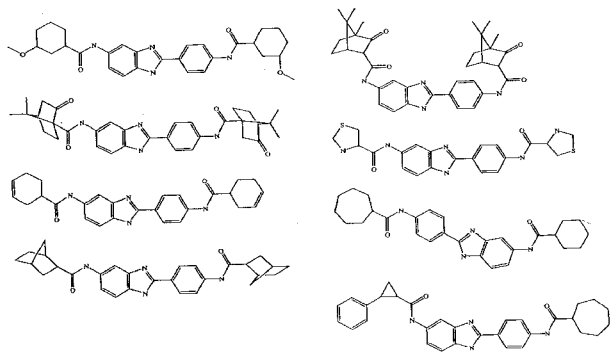

Column 31,
The following formulas should be deleted:

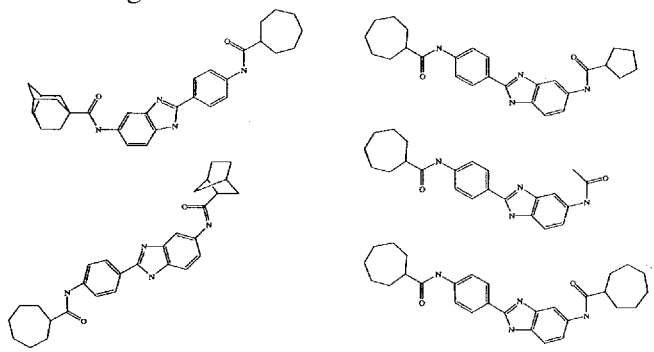

UNITED STATES PATENT AND TRADEMARK OFFICE
CERTIFICATE OF CORRECTION

PATENT NO. : 6,369,091 B1
DATED : April 9, 2002
INVENTOR(S) : Sicar et al.

It is certified that error appears in the above-identified patent and that said Letters Patent is hereby corrected as shown below:

Column 32,
The following formula should be deleted:

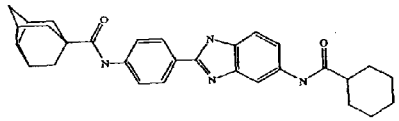

Column 33,
The following formulas should be deleted:

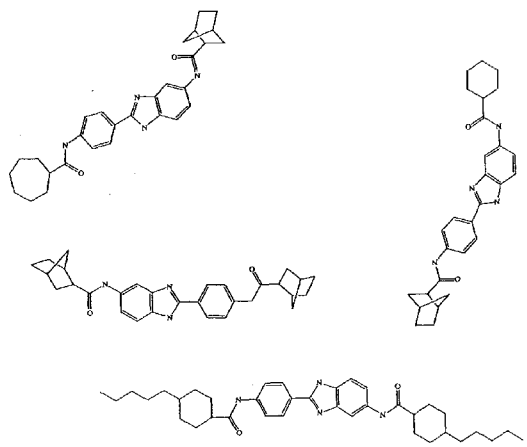

Column 34,
The following formulas should be deleted:

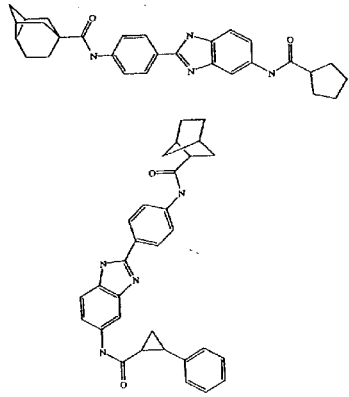

UNITED STATES PATENT AND TRADEMARK OFFICE
CERTIFICATE OF CORRECTION

PATENT NO. : 6,369,091 B1  Page 6 of 10
DATED : April 9, 2002
INVENTOR(S) : Sicar et al.

It is certified that error appears in the above-identified patent and that said Letters Patent is hereby corrected as shown below:

Column 35,
The following formulas should be deleted:

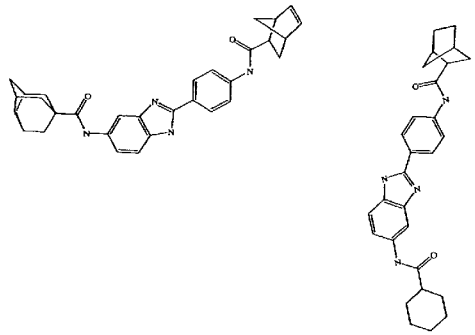

Column 36,
The following formulas should be deleted:

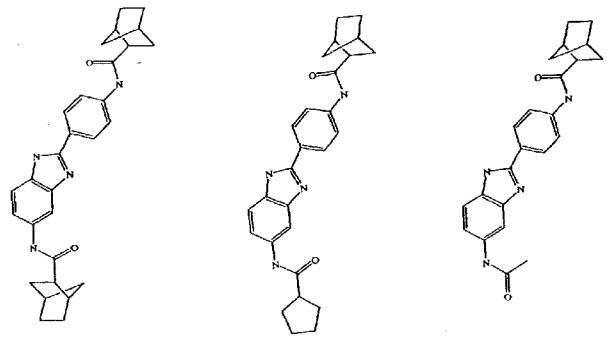

Column 37,
The following formulas should be deleted:

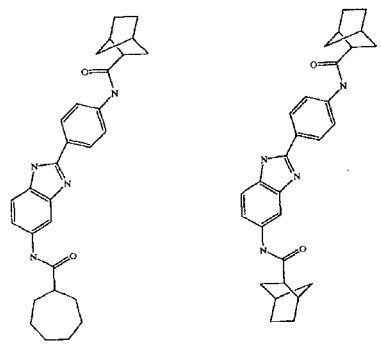

UNITED STATES PATENT AND TRADEMARK OFFICE
CERTIFICATE OF CORRECTION

PATENT NO.    : 6,369,091 B1                                          Page 7 of 10
DATED         : April 9, 2002
INVENTOR(S)   : Sicar et al.

It is certified that error appears in the above-identified patent and that said Letters Patent is hereby corrected as shown below:

Column 38,
The following formula should be deleted:

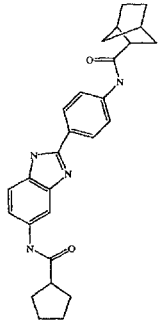

Column 39,
The following formulas should be deleted:

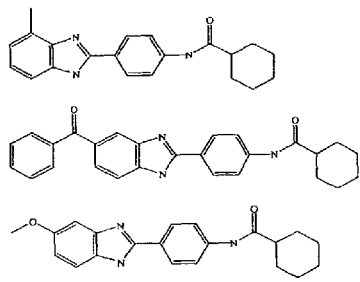

Column 40,
The following formulas should be deleted:

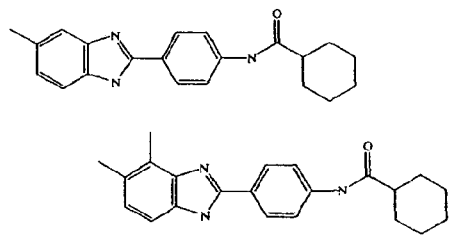

UNITED STATES PATENT AND TRADEMARK OFFICE
CERTIFICATE OF CORRECTION

PATENT NO. : 6,369,091 B1  Page 8 of 10
DATED : April 9, 2002
INVENTOR(S) : Sicar et al.

It is certified that error appears in the above-identified patent and that said Letters Patent is hereby corrected as shown below:

Column 44,
Lines 45-50, the formula should be deleted.

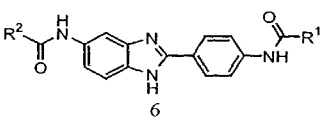

Column 47,
Line 5, the formula 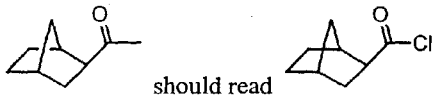 should read 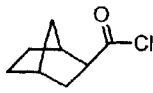.

Line 6, the formula 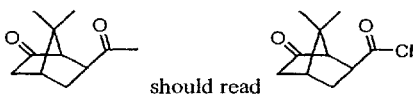 should read 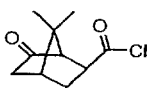

Column 48,
Line 5, the formula 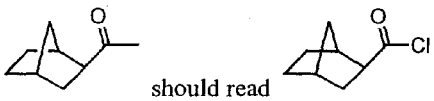 should read 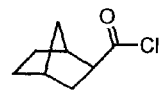.

Line 6, the formula 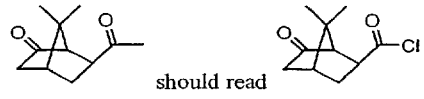 should read 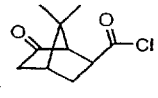

Column 73,
Line 2, the portion of the label corresponding to formula

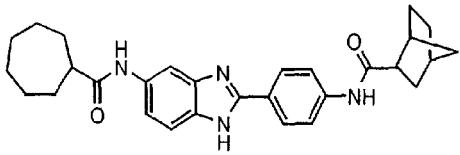 should read S-20.

Column 74,
Line 2, the portion of the label corresponding to formula

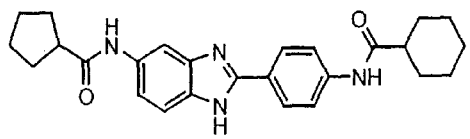 should read S-21.

UNITED STATES PATENT AND TRADEMARK OFFICE
CERTIFICATE OF CORRECTION

PATENT NO. : 6,369,091 B1
DATED : April 9, 2002
INVENTOR(S) : Sicar et al.

It is certified that error appears in the above-identified patent and that said Letters Patent is hereby corrected as shown below:

Column 79,
Line 2, the portion of the label corresponding to formula

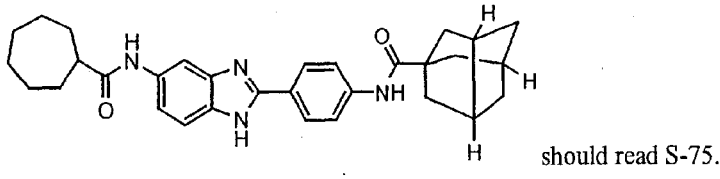 should read S-75.

Line 3, the portion of the label corresponding to formula

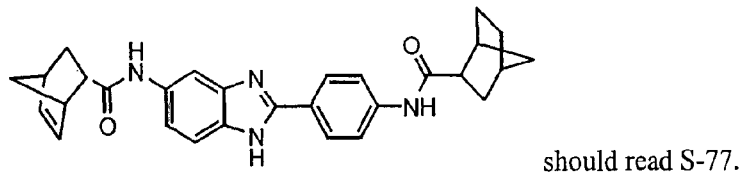 should read S-77.

Column 80,
Line 2, the portion of the label corresponding to formula

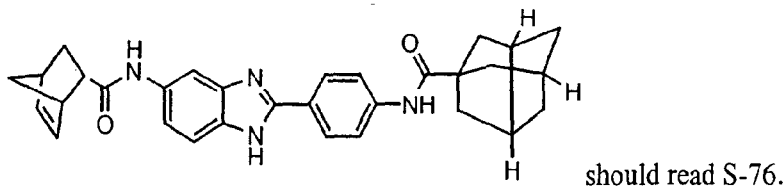 should read S-76.

UNITED STATES PATENT AND TRADEMARK OFFICE
CERTIFICATE OF CORRECTION

PATENT NO. : 6,369,091 B1
DATED : April 9, 2002
INVENTOR(S) : Sicar et al.

It is certified that error appears in the above-identified patent and that said Letters Patent is hereby corrected as shown below:

Column 80 cont'd,
Line 3, the portion of the label corresponding to formula

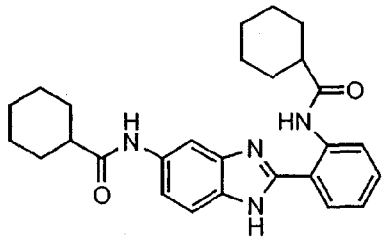 should read S-79.

Signed and Sealed this

Twenty-sixth Day of November, 2002

Attest:

JAMES E. ROGAN
Attesting Officer  Director of the United States Patent and Trademark Office

UNITED STATES PATENT AND TRADEMARK OFFICE
CERTIFICATE OF CORRECTION

| | | |
|---|---|---|
| PATENT NO. | : 6,369,091 B1 | Page 1 of 1 |
| APPLICATION NO. | : 09/422304 | |
| DATED | : April 9, 2002 | |
| INVENTOR(S) | : Jagadish C. Sircar et al. | |

It is certified that error appears in the above-identified patent and that said Letters Patent is hereby corrected as shown below:

Page 1, Col. 1, line (60): The filing date for Provisional Application No. 60/086,494 should be changed from "May 21, 1998" to --May 22, 1998,--

Signed and Sealed this

Twenty-sixth Day of June, 2007

JON W. DUDAS
*Director of the United States Patent and Trademark Office*